(12) United States Patent
Boyden et al.

(10) Patent No.: US 9,493,784 B2
(45) Date of Patent: *Nov. 15, 2016

(54) PEPPER PLANTS AND FRUITS WITH IMPROVED NUTRITIONAL VALUE

(75) Inventors: Laurie Boyden, Stanton, MN (US); Kevin Cook, Naples, FL (US); Steven John Czaplewski, Naples, FL (US); Henricus Johannes Van Wijk, Saint-Sauveur (NL)

(73) Assignee: Syngenta Participations AG, Basel (CH)

(*) Notice: Subject to any disclaimer, the term of this patent is extended or adjusted under 35 U.S.C. 154(b) by 142 days.

This patent is subject to a terminal disclaimer.

(21) Appl. No.: 14/241,613

(22) PCT Filed: Sep. 7, 2012

(86) PCT No.: PCT/EP2012/067585
§ 371 (c)(1),
(2), (4) Date: Apr. 1, 2014

(87) PCT Pub. No.: WO2013/034747
PCT Pub. Date: Mar. 14, 2013

(65) Prior Publication Data
US 2014/0230102 A1  Aug. 14, 2014

(30) Foreign Application Priority Data
Sep. 8, 2011  (EP) .................................. 11180586

(51) Int. Cl.
| | | |
|---|---|---|
| *C12Q 1/68* | (2006.01) | |
| *A01H 1/04* | (2006.01) | |
| *A01H 5/08* | (2006.01) | |
| *C12N 15/82* | (2006.01) | |

(52) U.S. Cl.
CPC ............... *C12N 15/825* (2013.01); *A01H 1/04* (2013.01); *A01H 5/08* (2013.01); *C12Q 1/6895* (2013.01)

(58) Field of Classification Search
None
See application file for complete search history.

(56) References Cited

U.S. PATENT DOCUMENTS

2011/0197313 A1*  8/2011  Lindeman ................ A01H 5/08
800/279

OTHER PUBLICATIONS

Lee et al. Journal of Food Science 60(3): 473-476 (1995).*

Ozores-Hampton et al. University of Florida/SWFREC Report, pp. 1-10 (Mar. 2011).*
Trade Winds Fruit Company Catalog, Ancho San Luis Pepper, available prior to Aug. 2011.*
Wahyuni et al. Phytochemistry 72(11-12): 1358-1370 (Aug. 2011).*
Lee et al., "Flavonoids and antioxidant activity of fresh pepper (Capsicum annuum) cultivars", Journal of Food Science, 60, Jan. 1, 1995, pp. 473-476.
Camara et al., "Free and esterified carotenoids in green and red fruits of Capsicum annuum", hytochemistry, Pergmon Press, GB, 17(1), Jan. 1 1978, pp. 91-93.
Minguez-Mosquera et al., "Formation and transformation of pigments duing the furit rpening of Capsicum annuum cv. Bola and Agridulce," Jouornal of Agricultural and Food Chemistry, American Chemical Society, US., 42(1), Jan. 1, 1994, pp. 38-44.
Chaim et al., "QTL mapping of fruit-related traits ain pepper (Capsicum annuum)," Theoretical and Applied Genetics, vol. 102, Jan. 1, 2001, pp. 1016-1028.
Brand et al., "pc8.1, a major QTL for pigment content in pepper furit is associated with variation in plastid compartment size," Pinta, Oct. 11, 2011.
Hornero-Mendez et al., "Carotenoid biosynthesis changes in five red pepper (Capsicum annuum L.) cultivars during rpening. Cultivar selection for breeding," Journal of Agricultural and Food Chemistry, American Chemical Society, U.S., 48(9), Sep. 1, 2000, pp. 3857-3864.
Lightbourn et al., "Effects of Anthocyanin and Carotenoid combinations on foliage and and immature fruit color Capisicum annuum L. ," Journal of Heredity, 99(2), Jan. 24, 2008, pp. 105-111.
Ji-Sun Kim et al., "Phytochemicals and antioxidant activity of fruits and leaves of paprika (Capsicum Annuum L., var. special) Cultivated in Kore," Journal of Food Science, 76(2), Jan. 21, 2011, pp. C193-C198.
Borovsky et al., "Chlorophyll breakdown during pepper furit ripening in the chlorophyll retainer mutation is impaired at the homolog of the senescence-inducible stay-green gene," Theoretical and Applied Genetics, Interntional Journal of Plant Breeding Research, Springer, Berlin, DE, 117(2), Apr. 22, 2008, pp. 235-240.
International Search Report dated Nov. 20, 2012 for International Patent Application No. PCT/EP2012/067585.
International Preliminary Report on Patentability dated Mar. 12, 2014 for International Patent Application No. PCT/EP2012/067585.

* cited by examiner

*Primary Examiner* — David T Fox
(74) *Attorney, Agent, or Firm* — Karen A. Magri

(57) ABSTRACT

The present invention concerns *Capsicum annuum* plants producing pepper fruits, exhibiting new physicochemical characteristics of the pepper fruit in relation with chlorophyll A & B, lutein as well as violaxanthin. The pepper fruits of the plants according to the present invention also exhibit a characteristic extreme dark green color at immature stage which color is linked to the content in pigment of the said fruit. The present invention also relates to QTL alleles directing the expression of the pigment content of those pepper fruits as well as molecular markers associated with these QTL alleles.

2 Claims, 4 Drawing Sheets

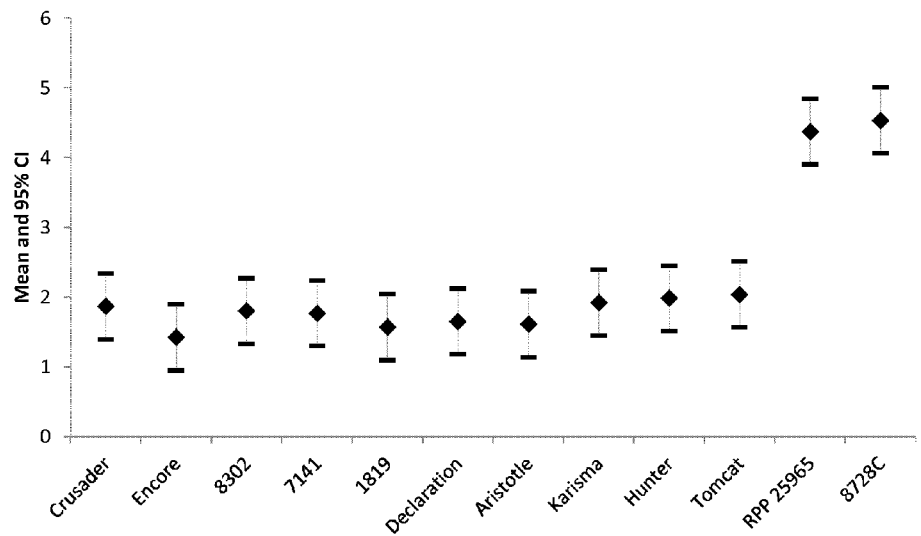
Figure 1 - Violaxanthin
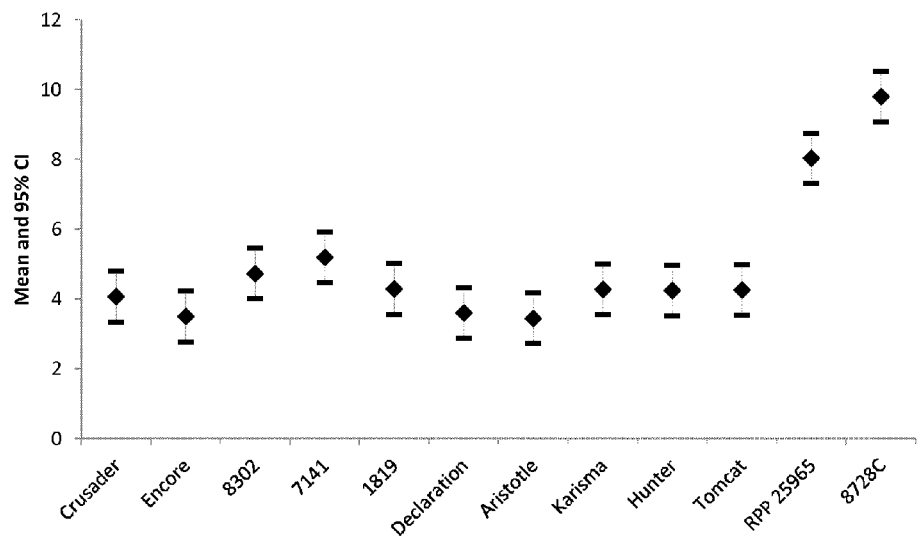
FIGURE 2 - Lutein

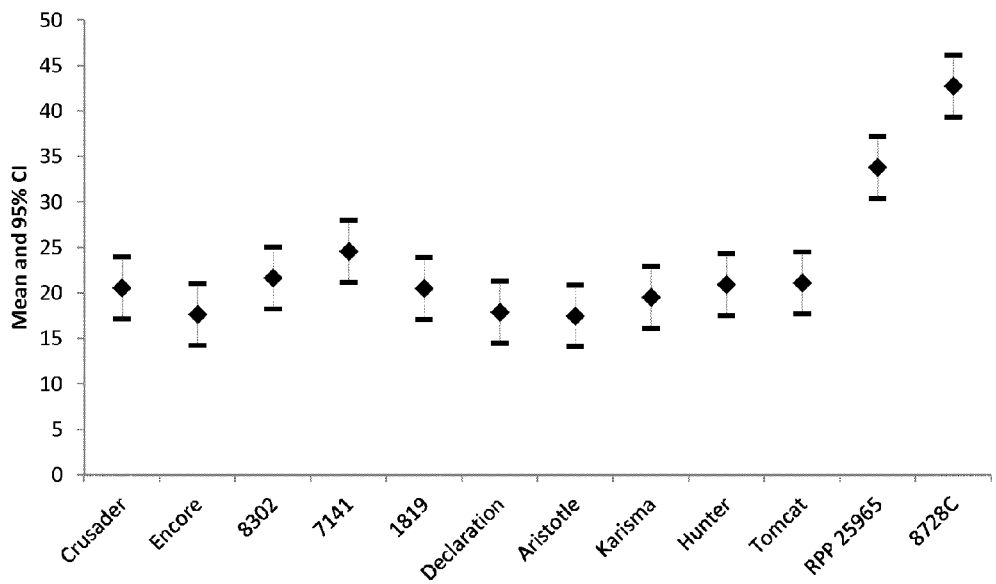
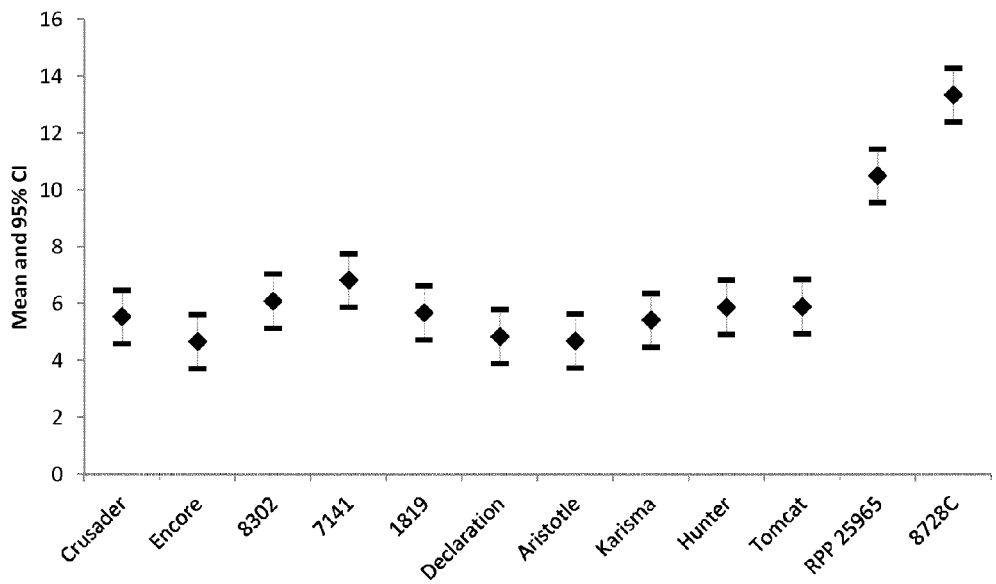

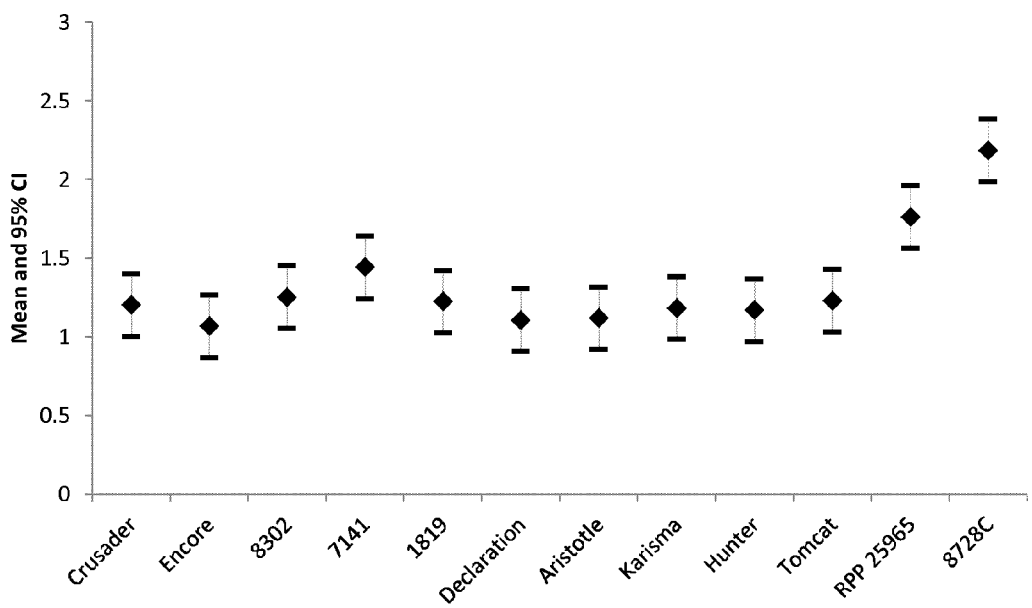
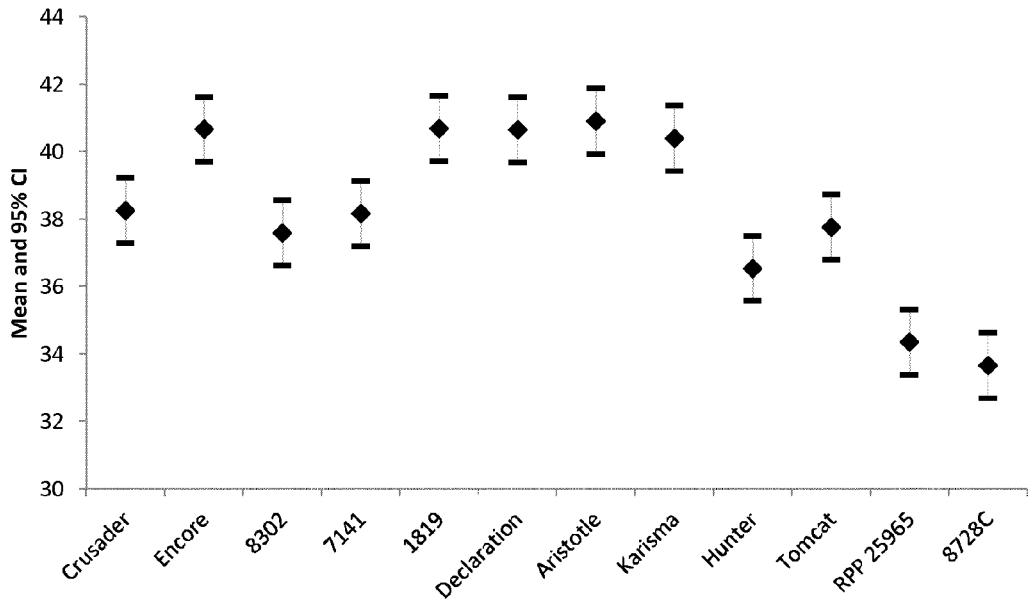

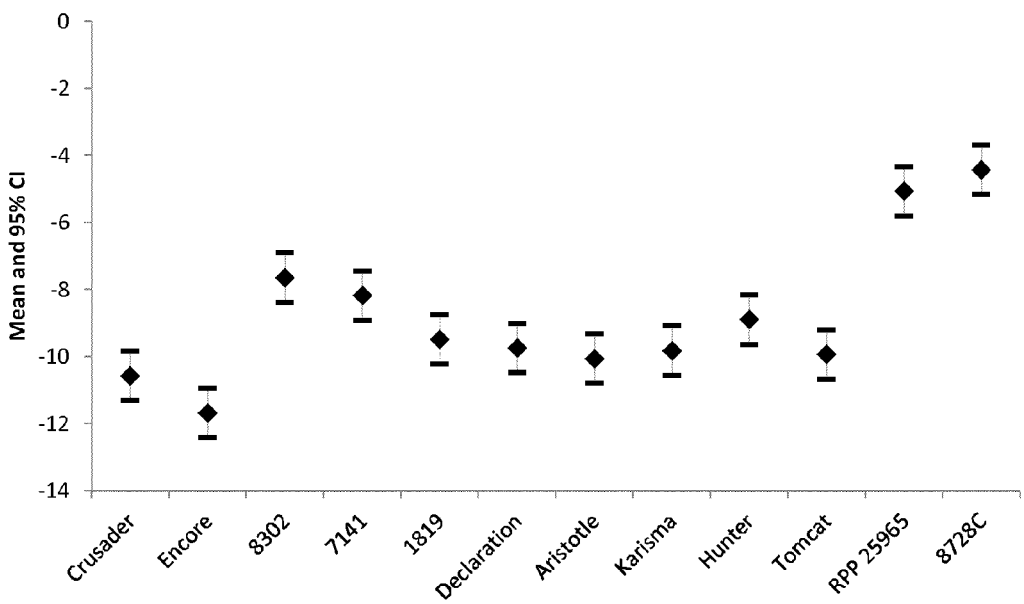
FIGURE 7 -a*(C)
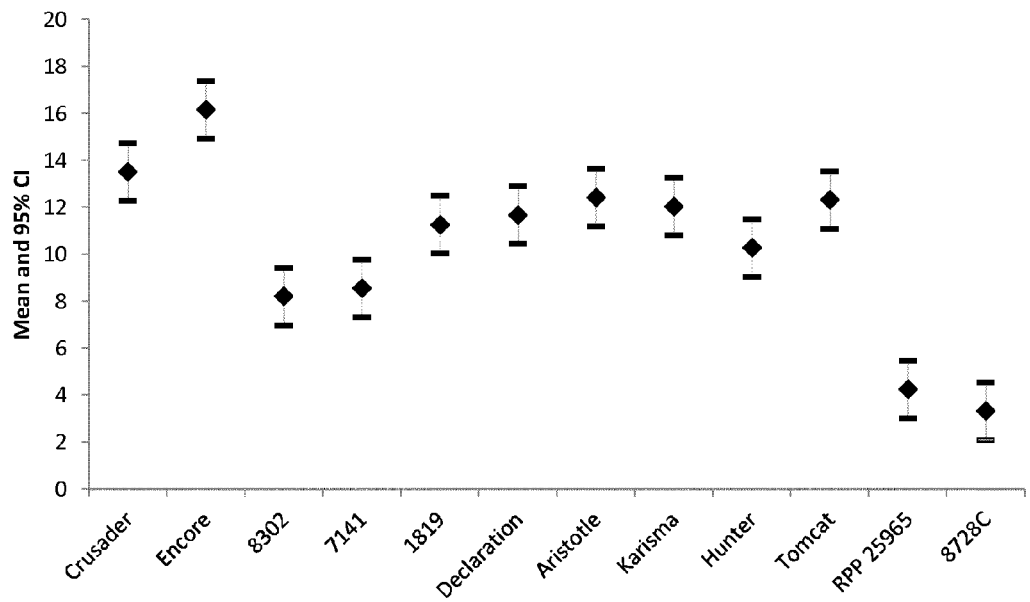
FIGURE 8 -b*(C)

PEPPER PLANTS AND FRUITS WITH IMPROVED NUTRITIONAL VALUE

RELATED APPLICATION INFORMATION

This application claims priority under 35 U.S.C. §371 from PCT Application No. PCT/EP2012/067585, filed Sep. 7, 2012, which claims the benefit of European Application No. 11180586.7, filed Sep. 8, 2011, the disclosures of which are incorporated by reference herein in their entirety.

FIELD OF THE INVENTION

The present invention includes pepper plants producing pepper fruits with enhanced green color and methods for obtaining such pepper plants. The present invention also provides molecular tools that can be used in methods for obtaining such pepper plants and such pepper fruits.

BACKGROUND OF THE INVENTION

Fruits of plants of the genus *Capsicum*, like sweet peppers and hot peppers, hereafter both types being referred to as peppers, are available in a wide variety of different colors like red, yellow, brown, and orange generally for fully matured fruits and green, white, lilac, and purple for non-mature "unripe" fruits.

Chlorophyll is the molecule that is called a photoreceptor. It is found in the chloroplasts of green pepper plants, and is what makes pepper fruits green. The basic structure of a chlorophyll molecule is a porphyrin ring, coordinated to a central atom. This is very similar in structure to the heme group found in hemoglobin, except that in heme the central atom is iron, whereas in chlorophyll it is magnesium.

It is usually easy to tell when a food has significant amounts of chlorophyll, because chlorophyll provides the green color that is found in the green parts of the plants and in many of the fruits and vegetables that are consumed. These plants and foods would not be green without their chlorophyll, since chlorophyll pigments reflect sunlight at exact appropriate wavelengths for our eyes to detect them as green. The chlorophyll a molecule actually reflects light in a blue-green range (about 685 nanometer wavelengths), while chlorophyll b reflects light in a more yellow-green color (about 735 nanometer wavelengths). The overall effect, however, is a color that one would simply call "green."

All green plants contain chlorophyll a, and most vegetables that are eaten contain both chlorophyll a and chlorophyll b, while in many of them, there is slightly more chlorophyll a than chlorophyll b and this slight edge in favor of chlorophyll a tends to decrease as the plant ages. Some vegetables contain particularly high amounts of total chlorophyll. Best studied of all the vegetables is spinach containing about 300-600 milligrams per ounce.

Among vegetables consumed around the world—asparagus, green bell peppers, broccoli, Brussels sprouts, green cabbage, celery, collard greens, green beans, green peas, kale, leeks, green olives, parsley, romaine lettuce, sea vegetables, spinach, Swiss chard, and turnip greens are concentrated sources of chlorophyll.

Research on the health benefits of chlorophyll has focused on the area of cancer. This research got underway when damage to genes by carcinogenic substances called aflatoxins, was found to be prevented by chlorophyllin, a derivative of chlorophyll. Research studies in humans (Egner et al. 2001 and 2003, Jubert et al. 2009) have found that damage to DNA by aflatoxin can be decreased as much as 55% through supplementation with chlorophyllin at 100 milligrams, three times a day, for four months. This amount of chlorophyllin, 300 milligrams per day, is the same amount of chlorophyll found in one weighted ounce of spinach (a little over ½ cup of chopped raw spinach). Although research is still in the early stage, prevention and treatment of liver cancer, skin cancer, and colon cancer are all being investigated in relationship to intake of chlorophyll-containing vegetables and supplementation with chlorophyllin.

Another study by Chernomorsky and his colleagues (Chernomorsky et al. 1999) addressed the preventive effect of chlorophyll and derivatives. The growing body of epidemiological and experimental evidence associating diets rich in fruits and vegetables with prevention of chronic diseases such as cancer has stimulated interest in plant food phytochemicals as physiologically active dietary components. Chlorophyll and its various derivatives are believed to be among the family of phytochemical compounds that are potentially responsible for such associations. Dietary chlorophyll is predominantly composed of lipophilic derivatives including chlorophyll a and b (fresh fruits and vegetables), metal-free pheophytins and pyropheophytins (thermally processed fruits and vegetables), as well as Zn-pheophytins and Zn-pyropheophytins (thermally processed green vegetables). Although the use of chlorophyll derivatives in traditional medical applications is well documented, it is perhaps the potential of chlorophyll as a cancer preventative agent that has drawn significant attention recently. Biological activities attributed to chlorophyll derivatives consistent with cancer prevention include antioxidant and antimutagenic activity, mutagen trapping, modulation of xenobiotic metabolism, and induction of apoptosis. Recent research efforts have also included investigation of the impact of digestive factors on chlorophyll structure and bioaccessibility as a means to better understand the extent to which these pigments may be bioavailable in humans and therefore may have more systemic impact in the prevention of cancer (Ferruzzi and Blakeslee, 2007).

It has been recognized that the perception of food products, particularly fresh vegetables, is highly impacted by the color of the said product. In vegetable products like pepper or tomato, intensity of red color can be perceived as a sign of intense flavor while the green color as seen for salad, broccoli and green pepper is perceived as a sign of freshness and healthiness of the product. Indeed, the greener is the product, the fresher and healthier it is perceived.

The plant pigments lutein and zeaxanthin are antioxidants. Good sources of lutein and zeaxanthin include a variety of vegetables as well as other foods. Fresh, raw foods are best when it comes to getting the most nutrition per serving.

A study conducted by the Journal of the American College of Nutrition in 2004 concluded that "There is a continuously growing body of evidence that suggests that lutein and zeaxanthin may contribute to the protection against several age-related diseases, including cataract and age-related macular degeneration as well as other diseases including dementia." Vegetables are by far the greatest source of lutein and zeaxanthin. Leafy greens such as romaine, spinach, Swiss chard, turnip greens, kale, collard greens, watercress and parsley top the content list. Fresh red and orange peppers also offer suitable source of lutein. According to the American Optometric Association, both lutein and zeaxanthin are of great benefit to eye health. Along with helping to prevent age-related macular degeneration (AMD), they can also improve vision in those already afflicted with this disease; they decrease the risk of contracting cataracts too, since both of these carotenoids protect and maintain healthy cells in the eye. Other health benefits are protection of your heart and brain, and they assist the body in combating arthritis as well.

Violaxanthin maybe a metabolite or precursor of zeaxanthin depending of sun light exposure and the amount of the first one may be a good indicator of the amount of the second one.

Peppers represent a valuable source of vitamins and nutrients associated with their pigments and fruit color, including various antioxidants, carotenoids as well as chlorophyll. In the present trend of consumers looking for fresh and healthy vegetables, pepper fruits constitute a product of choice.

Peppers fruits are generally green when immature and turn generally red, orange, or yellow once mature. The color of the pepper fruits is a result of a mixture of different color components in the fruit. The color component green is provided by the presence of chloroplasts containing an abundant amount of chlorophyll. The color components red and yellow are provided by chromoplasts filled with red and yellow carotenoids, respectively. Examples of such carotenoids are capsanthin and capsorubin, lutein, beta carotene, violaxanthin and zeaxanthin. The different possible colors of the immature and mature fruits are usually a combination of different ratios between the different chlorophyll and carotenoids pigments.

In some of the markets, peppers are usually harvested green, i.e. at a non mature stage. Immature pepper fruits generally exhibit a less sweet taste as compared to red-mature-fruits.

Immature green peppers fruits can exhibit various green color variations from very pale green to dark green. Higher intensity of the green pepper color is considered as a sign of freshness and quality by consumers as well as perceived as a health attribute. It is then a continuous and vigorous trend from consumers to get green pepper fruits exhibiting a deep and intense green color.

It is therefore a need to provide pepper plants that produce pepper fruits with enhanced deep and intense green color, associated with enhanced nutritional value thanks to enhanced antioxidants, carotenoids and other healthy compounds content as well as a green color appearance that would render them attractive to the consumer, with enhanced perception of freshness and quality.

SUMMARY OF THE INVENTION

The present invention includes and provides pepper plants having extreme dark green color pepper fruits at immature harvestable stage that also exhibit high content in pigments.

Indeed, it has been surprisingly found by the inventors of the present invention that the increase of the quantity of selected pigments like chlorophyll A & B, lutein as well as violaxanthin is also accompanied by a modification of the external color perception of the pepper fruit at immature harvestable stage. The fruits of the pepper plant of the present invention thus exhibit an extreme dark green color that could be called extreme dark green or extreme green and that can be either measured by colorimeter parameters or by eye-measurement. The pepper plant according to the present invention thus produces fruits with enhanced nutritional properties thanks to increase content in Chlorophyll A & B, lutein and violaxanthin as compared to various pepper plants available on the market and additionally the said fruits can also be recognized and identified visually thank to the particular and characteristic color when marketed at immature green stage.

In one embodiment, the pepper fruits are blocky type pepper fruits.

In one embodiment, is provided a cultivated *Capsicum annuum* plant producing pepper fruits, particularly a blocky type pepper plant producing blocky type pepper fruits exhibiting extreme dark green color at immature harvestable stage, characterized by the following physicochemical characteristics of the pepper fruit:
  a content in Chlorophyll B greater than 6, particularly greater than 7, more particularly greater than 8 and even more particularly greater than 9 µg/g of fresh weight,
  a content in Chlorophyll A greater than 20, particularly greater than 25, more particularly greater than 30 µg/g of fresh weight,
  a content in lutein greater than 5, particularly greater than 6, more particularly greater than about 7 µg/g of fresh weight,
  a content in violaxanthin greater than 2, particularly greater than 2.5, more particularly greater than 3, even more particularly greater than 3.5 µg/g of fresh weight, Those physicochemical values have been found characteristic of the so called extreme dark color of the pepper plant according to the present invention.

In the remaining part of the description the expression "extreme dark green color" or "extreme dark green allele", "extreme dark green locus" or "extreme dark green trait" is equated to the physicochemical characteristics of the pepper fruits at immature harvestable stage as described above, i.e.:
  a content in Chlorophyll B greater than 6, particularly greater than 7, more particularly greater than 8 and even more particularly greater than 9 µg/g of fresh weight,
  a content in Chlorophyll A greater than 20, particularly greater than 25, more particularly greater than 30 µg/g of fresh weight,
  a content in lutein greater than 5, particularly greater than 6, more particularly greater than about 7 µg/g of fresh weight,
  a content in violaxanthin greater than 2, particularly greater than 2.5, more particularly greater than 3, even more particularly greater than 3.5 µg/g of fresh weight, The present invention includes and provides seed of the pepper plant 8728C where a representative sample of seed of the variety has been deposited under NCIMB Accession No NCIMB 41858 on Jul. 29, 2011.

The present invention also includes and provides methods of introgressing at least one, preferably two, extreme dark green pepper fruit QTL allele(s) associated with enhanced choloropyll A, chlorophyll B, lutein and violaxanthin contents into a pepper plant comprising:
  a) crossing a plant from a first pepper plant as a first parent having at least one, preferably two, extreme dark green pepper fruit allele(s) with a second pepper plant as a second parent aiming to form a population segregating for dark green immature fruit color,
  b) phenotyping the population aiming to select plants with darker immature fruit color having one, preferably two, extreme dark green fruit QTL allele(s),
  c) screening the segregating population for a member having one, preferably two, extreme dark green pepper fruit QTL allele using (a) nucleic acid molecule(s) capable of identifying (an) extreme dark green allele(s), And d) selecting a pepper plant that contains one, preferably two, extreme dark green allele(s) at (a) QTL for further crossing.

The present invention further includes and provides methods of producing a pepper plant bearing extreme dark green pepper fruits comprising:
a) providing a pepper plant as a first parent;
b) crossing the first parent with a second pepper plant selected from the group consisting of pepper plants producing pepper fruits, particularly a blocky type pepper plant producing blocky type pepper fruits exhibiting extreme dark green color at immature harvestable stage, characterized by the following physicochemical characteristics of the pepper fruits:
  i. a content in Chlorophyll B greater than 6, particularly greater than 7, more particularly greater than 8 and even more particularly greater than 9 µg/g of fresh weight,
  ii. a content in Chlorophyll A greater than 20, particularly greater than 25, more particularly greater than 30 µg/g of fresh weight,
  iii. a content in lutein greater than 5, particularly greater than 6, more particularly greater than about 7 µg/g of fresh weight,
  iv. a content in violaxanthin greater than about 2, particularly greater than 2.5, more particularly greater than 3, even more particularly greater than 3.5 µg/g of fresh weight,
c) growing pepper plant seed produced by the cross to yield a progeny pepper plant bearing fruits;
d) determining chlorophyll a content, chlorophyll b content, lutein content, violaxanthin content for the pepper fruits of progeny pepper plants of c;
e) selecting the progeny pepper plant(s) that has pepper fruits with the following physicochemical characteristics:
  i. a content in Chlorophyll B greater than 6, particularly greater than 7, more particularly greater than 8 and even more particularly greater than 9 µg/g of fresh weight,
  ii. a content in Chlorophyll A greater than 20, particularly greater than 25, more particularly greater than 30 µg/g of fresh weight,
  iii. a content in lutein greater than 5, particularly greater than 6, more particularly greater than about 7 µg/g of fresh weight,
  iv. a content in violaxanthin greater than 2, particularly greater than 2.5, more particularly greater than 3, even more particularly greater than 3.5 µg/g of fresh weight, thereby producing a pepper plant bearing extreme dark green pepper fruits at immature harvestable stage.

The present invention also includes and provides a pepper plant bearing extreme dark green color fruit at immature harvestable stage, said plant comprising two genetic determinant directing or controlling expression of said extreme dark green color in the pepper fruit of the pepper plant, wherein said genetic determinants are obtainable from a pepper plant source, particularly from *Capsicum annuum*, particularly from *Capsicum annuum* 8728C seed of which has been deposited under Deposit Number NCI MB 41858 on Jul. 29, 2011.

The extreme dark green color fruits at immature harvestable stage borne by the plant of the present invention are characterized by:
a. a content in Chlorophyll B greater than 6, particularly greater than 7, more particularly greater than 8 and even more particularly greater than 9 µg/g of fresh weight,
b. a content in Chlorophyll A greater than 20, particularly greater than 25, more particularly greater than 30 µg/g of fresh weight,
c. a content in lutein greater than 5, particularly greater than 6, more particularly greater than about 7 µg/g of fresh weight,
d. a content in violaxanthin greater than 2, particularly greater than 2.5, more particularly greater than 3, even more particularly greater than 3.5 µg/g of fresh weight, The genetic determinant(s) that controls the expression of the extreme dark green color in the pepper fruits also control the following physicochemical characteristics:
a content in Chlorophyll B greater than 6, particularly greater than 7, more particularly greater than 8 and even more particularly greater than 9 µg/g of fresh weight,
a content in Chlorophyll A greater than 20, particularly greater than 25, more particularly greater than 30 µg/g of fresh weight,
a content in lutein greater than 5, particularly greater than 6, more particularly greater than about 7 µg/g of fresh weight,
a content in violaxanthin greater than 2, particularly greater than 2.5, more particularly greater than 3, even more particularly greater than 3.5 µg/g of fresh weight, The present invention further includes and provides methods of identifying a pepper plant bearing extreme dark green trait pepper fruits at immature harvestable stage associated with the following physicochemical characteristics:
a. a content in Chlorophyll B greater than 6, particularly greater than 7, more particularly greater than 8 and even more particularly greater than 9 µg/g of fresh weight,
b. a content in Chlorophyll A greater than 20, particularly greater than 25, more particularly greater than 30 µg/g of fresh weight,
c. a content in lutein greater than 5, particularly greater than 6, more particularly greater than about 7 µg/g of fresh weight,
d. a content in violaxanthin greater than 2, particularly greater than 2.5, more particularly greater than 3, even more particularly greater than 3.5 µg/g of fresh weight,
comprising:
a) providing a population segregating for extreme dark green immature fruit color,
b) screening the genome of segregating population for a member having an extreme dark green pepper fruit trait, wherein said trait can be identified by the presence of the following molecular markers in the genome: SP436, SP626, SP693 and SP694,
c) selecting one member of the segregating population, wherein said member is bearing one extreme dark green pepper fruit trait and comprises the molecular markers of b).

DETAILED DESCRIPTION OF THE INVENTION

Embodiments

In a 1<sup>st</sup> embodiment, the invention relates to a pepper plant, particularly a cultivated pepper plant, more particularly a cultivated blocky fruit type pepper plant, bearing extreme dark green color fruit at immature harvestable stage, said plant comprising two genetic determinants directing or controlling expression of said extreme dark green color in the pepper fruit of the pepper plant.

In particular, in a specific embodiment, said two genetic determinants are represented by two QTL or a functional part thereof capable of directing or controlling expression of said dark green immature fruit color in the pepper fruit of the pepper plant.

The extreme "dark green color" or "extreme dark green trait" is associated with the following physicochemical characteristics of the pepper fruits at immature harvestable stage of the pepper plant of the invention:
  a content in Chlorophyll B greater than 6, particularly greater than 7, more particularly greater than 8 and even more particularly greater than 9 µg/g of fresh weight,
  a content in Chlorophyll A greater than 20, particularly greater than 25, more particularly greater than 30 µg/g of fresh weight,
  a content in lutein greater than 5, particularly greater than 6, more particularly greater than about 7 µg/g of fresh weight,
  a content in violaxanthin greater than 2, particularly greater than 2.5, more particularly greater than 3, even more particularly greater than 3.5 µg/g of fresh weight, In one embodiment, a pepper plant according to previous embodiment is provided, particularly a cultivated pepper plant, wherein two QTL or a functional part thereof are genetically or physically linked to four marker loci, which co-segregate with the extreme dark green color and are selected in the group comprising: SP436, SP626, SP693 and SP694.

In one embodiment, the first QTL, QTL1, is genetically or physically linked to marker loci SP436 and SP626 and the second QTL, QTL2, is linked to marker loci SP693 and SP694.

In one embodiment, a pepper plant, particularly a cultivated pepper plant, according to any of the preceding embodiments is provided, wherein said QTL1 or a functional part thereof is genetically linked to two marker loci and wherein:
  i. marker locus SP436 can be identified in a PCR by amplification of a DNA fragment with the pair of oligonucleotide primers: forward primer of SEQ ID NO: 1 and reverse primer of SEQ ID NO: 2 and probe SEQ ID NO 9,
  ii. marker locus SP626 can be identified in a PCR by amplification of a DNA fragment with the pair of oligonucleotide primers: forward primer of SEQ ID NO: 3 and reverse primer of SEQ ID NO: 4 and probe SEQ ID NO 10.

In one embodiment, a pepper plant, particularly a cultivated pepper plant, according to any of the preceding embodiments is provided, wherein said QTL2 or a functional part thereof is genetically linked to two marker loci, and wherein:
  i. marker locus SP693 can be identified in a PCR by amplification of a DNA fragment with the pair of oligonucleotide primers: forward primer of SEQ ID NO: 5 and reverse primer of SEQ ID NO: 6 and probe SEQ ID NO 11,
  ii. marker locus SP694 can be identified in a PCR by amplification of a DNA fragment with the pair of oligonucleotide primers: forward primer of SEQ ID NO: 7 and reverse primer of SEQ ID NO: 8 and probe SEQ ID NO 12.

In one embodiment, the invention relates to a pepper plant, particularly a cultivated pepper plant, according to any of the preceding embodiments, comprising two allele at two quantitative trait locus in the pepper genome contributing to extreme dark green color in the pepper fruit of the pepper plant, which are complementary to the corresponding alleles present in *Capsicum annuum*, line 8728C, seed of which is deposited under Deposit Number NCIMB 41858 on Jul. 29, 2011, or in the progeny or in an ancestor thereof, and genetically linked to four marker loci in the genome of *Capsicum annuum*, line 8728C, seed of which has been deposited at NCIMB under No NCI MB 41858 on Jul. 29, 2011, or in the progeny or in an ancestor thereof, which marker loci co-segregate with the Extreme dark green colour and can be identified in the genome of *Capsicum annuum*, line 8728C, seed of which has been deposited at NCIMB under No NCIMB 41858 on Jul. 29, 2011, and are selected in the group comprising SP436, SP626, SP693 and SP694.

In one embodiment of the invention, a pepper plant, particularly a cultivated pepper plant, according to any of the preceding embodiments is provided, wherein QTL1 is obtainable from a donor plant having the genetic background of *Capsicum annuum* 8728C, seed of which has been deposited under Deposit Number NCIMB under No NCIMB 41858 on Jul. 29, 2011, or in the progeny or in an ancestor thereof, comprising said QTL1 or a Extreme dark green color-conferring part thereof.

In one embodiment of the invention, a pepper plant, particularly a cultivated pepper plant, according to any of the preceding embodiments is provided, wherein QTL2 is obtainable from a donor plant having the genetic background of *Capsicum annuum* 8728C, seed of which has been deposited under Deposit Number NCI MB 41858 on Jul. 29, 2011, or in the progeny or in an ancestor thereof, comprising said QTL2 or a Extreme dark green color-conferring part thereof.

In one embodiment, a pepper plant, particularly a cultivated pepper plant, according to any of the preceding embodiments is provided, wherein said genetic determinants are obtainable from *Capsicum annuum* 8728C, seed of which has been deposited under Deposit Number NCIMB 41858 on Jul. 29, 2011.

In one embodiment of the invention, the pepper plant is a plant according to any of the preceding embodiments, which plant is a pepper plant of the genus *Capsicum*, particularly a cultivated pepper plant, particularly a haploid, a di-haploid, an inbred or a hybrid. In one embodiment, the invention provides a pepper plant according to any of the preceding embodiments, which is a hybrid pepper plant, particularly a cultivated pepper plant, comprising QTL1 and QTL2 or an Extreme dark green color-conferring part thereof and producing pepper fruits with the following physicochemical characteristic at immature harvestable stage:
  a. a content in Chlorophyll B greater than 6, particularly greater than 7, more particularly greater than 8 and even more particularly greater than 9 µg/g of fresh weight,
  b. a content in Chlorophyll A greater than 20, particularly greater than 25, more particularly greater than 30 µg/g of fresh weight,
  c. a content in lutein greater than 5, particularly greater than 6, more particularly greater than about 7 µg/g of fresh weight, d. a content in violaxanthin greater than 2, particularly greater than 2.5, more particularly greater than 3, even more particularly greater than 3.5 µg/g of fresh weight, wherein QTL1 and QTL2 are genetically linked to four marker loci co-segregating with the Extreme dark green color, wherein said QTL1 and QTL2 are obtainable from a donor plant having the genetic background of *Capsicum annuum* 8728C, seed of which has been deposited under Deposit Number NCIMB 41858 on Jul. 29, 2011, or in the progeny or in an ancestor thereof, comprising said QTL1 and QTL2 or a Extreme dark green color-conferring part thereof and wherein the four marker loci are selected in the group comprising SP436, SP626, SP693 and SP694.

In one embodiment the pepper plant, particularly a cultivated pepper plant, of the invention is a plant according to any of the preceding embodiments, which grows fruits selected from the group consisting of blocky type peppers.

The present invention further relates to seed of a pepper plant, particularly a cultivated pepper plant, according to any of the preceding embodiments, which is capable of growing a pepper plant bearing extreme dark green color fruit according to the invention.

In another embodiment, a kit for the detection of the Extreme dark green color locus in a pepper plant, particularly a cultivated pepper plant, is herein provided, wherein said kit comprises at least one PCR oligonucleotide primer pair and probe, selected from:
  a. primer pair 1 represented by a forward primer of SEQ ID NO 1 and a reverse primer of SEQ ID NO 2 and probe of SEQ ID NO 9 or;
  b. primer pair 2 represented by a forward primer of SEQ ID NO 3 and a reverse primer of SEQ ID NO 4 and probe of SEQ ID NO 10, or;
  c. primer pair 3 represented by a forward primer of SEQ ID NO 5 and a reverse primer of SEQ ID NO 6 and SEQ ID NO 11, or;
  d. primer pair 4 represented by a forward primer SEQ ID NO 7 and reverse primer of SEQ ID NO 8 and probe of SEQ ID NO 12, or
  another primer or primer pair representing an adjacent markers that is statistically correlated and thus co-segregates with the Extreme dark green color.

In a further embodiment, the present invention relates also to the use of some or all of these DNA markers/marker sequences according to the invention for diagnostic selection and/or genotyping of a pepper plant of the Extreme dark green color locus or loci in a pepper plant, particularly a cultivated pepper plant, particularly of the Extreme dark green color locus or loci, particularly in a pepper plant according to the invention.

In another embodiment, the present invention further contemplates the use of some or all of these DNA markers for identifying in a pepper plant, particularly a cultivated pepper plant, particularly a pepper plant according to the invention, the presence of the Extreme dark green color locus or loci and/or for monitoring the introgressing of the Extreme dark green color locus or loci in a pepper plant, particularly a cultivated pepper plant, particularly a pepper plant according to the invention and as described herein.

In one embodiment, the invention relates to the polynucleotide (amplification product) obtainable in a PCR reaction involving at least one oligonucleotide primer selected from the group consisting of SEQ ID NO 1; SEQ ID NO 2; SEQ ID NO 3; SEQ ID NO 4; SEQ ID NO 5; SEQ ID NO 6, SEQ ID NO 7; SEQ ID NO 8 or a pair of PCR oligonucleotide primers, and reacting with probes selected from the group comprising SEQ ID NO 9, SEQ ID NO 10, SEQ ID NO 11 and SEQ ID NO 12, selected from
  a. primer pair 1 represented by a forward primer of SEQ ID NO 1 and a reverse primer of SEQ ID NO 2, and probe of SEQ ID NO 9 or;
  b. primer pair 2 represented by a forward primer of SEQ ID NO 3 and a reverse primer of SEQ ID NO 4, and probe of SEQ ID NO 10 or;
  c. primer pair 3 represented by a forward primer of SEQ ID NO 5 and a reverse primer of SEQ ID NO 6, and probe of SEQ ID NO 11 or;
  d. primer pair 4 represented by a forward primer of SEQ ID NO 7 and a reverse primer of SEQ ID NO 8, and probe of SEQ ID NO 12 or
  by another primer representing an adjacent marker that is statistically correlated and thus co-segregates with the Extreme dark green color or with one of the markers disclosed, which amplification product corresponds to an amplification product obtainable from *Capsicum annuum* 8728C seed of which has been deposited under Deposit Number NCIMB 41858 on Jul. 29, 2011, in a PCR reaction with identical primers or primer pairs provided that the respective marker locus or loci is still present in said pepper plant and/or can be considered an allele thereof.

Also contemplated herein is a polynucleotide that has at least 90%, particularly at least 95%, particularly at least 96%, particularly at least 97%, particularly at least 98%, particularly at least 99% sequence identity with the sequence of said amplification product and/or a polynucleotide exhibiting a nucleotide sequence that hybridizes to the nucleotide sequences of said amplification product obtainable in the above PCR reaction.

The amplification product according to the invention and described herein above can then be used for generating or developing new primers and/or probes that can be used for identifying the Extreme dark green color locus.

The present invention therefore further relates in one embodiment to derived markers, particularly to derived primers or probes, developed from an amplification product according to the invention and as described herein above by methods known in the art, which derived markers are genetically linked to the Extreme dark green color locus, particularly the Extreme dark green color locus.

The identification of plant with extreme dark green color may be done by measuring and selecting plants bearing fruits with the following physicochemical characteristics at immature harvestable stage:
  a. a content in Chlorophyll B greater than 6, particularly greater than 7, more particularly greater than 8 and even more particularly greater than 9 µg/g of fresh weight,
  b. a content in Chlorophyll A greater than 20, particularly greater than 25, more particularly greater than 30 µg/g of fresh weight,
  c. a content in lutein greater than 5, particularly greater than 6, more particularly greater than about 7 µg/g of fresh weight,
  d. a content in violaxanthin greater than 2, particularly greater than 2.5, more particularly greater than 3, even more particularly greater than 3.5 µg/g of fresh weight, In a further embodiment, the invention relates to a method for producing a pepper plant, particularly a cultivated pepper plant, exhibiting extreme dark green color in the pepper fruit of the pepper plant, comprising the steps of:
  a. selecting a pepper plant of the genus *Capsicum annuum*, which exhibits Extreme dark green color, wherein said color related trait is associated with two QTL, QTL1 and QTL 2, or a functional part thereof capable of directing or controlling expression of said extreme dark green color in the pepper fruit of the pepper plant, wherein said QTL1 and QTL 2 or a functional part thereof are genetically linked to four marker loci, selected in the group comprising marker loci SP436, SP626, SP693 and SP694 or any adjacent marker that is statistically correlated and thus co-segregates with the Extreme dark green color, or with any of the disclosed markers loci, b. crossing said plant of step a), which exhibits Extreme dark green color, with a pepper plant, particularly a cultivated pepper plant, which is not extreme dark green color, and c. selecting progeny pepper plant from said cross which exhibits extreme dark green color and demonstrates association with said four marker loci of step a) and bears fruits with the following physicochemical characteristics at immature harvestable stage:
a. a content in Chlorophyll B greater than 6, particularly greater than 7, more particularly greater than 8 and even more particularly greater than 9 µg/g of fresh weight,
b. a content in Chlorophyll A greater than 20, particularly greater than 25, more particularly greater than 30 µg/g of fresh weight,
c. a content in lutein greater than 5, particularly greater than 6, more particularly greater than about 7 µg/g of fresh weight,
d. a content in violaxanthin greater than 2, particularly greater than 2.5, more particularly greater than 3, even more particularly greater than 3.5 µg/g of fresh weight.

In a further embodiment, the invention provides a method for obtaining pepper fruits with extreme dark green color, particularly blocky pepper fruits, comprising the steps of i. sowing a seed of a plant according to any one of the preceding embodiments or obtained in a method according to any of the preceding embodiments; and ii. growing said plant in order to produce fruit and harvesting the fruits produced by said plant.

The present invention further includes and provides methods of identifying a pepper plant bearing extreme dark green pepper fruits comprising:
a) providing a population segregating for dark green immature fruit color,
b) screening the segregating population for a member having an extreme dark green pepper fruit trait, wherein said trait can be identified by the presence of the following molecular markers in the genome: SP436, SP626, SP693 and SP694
c) selecting one member of the segregating population, wherein said member is bearing an extreme dark green pepper fruit trait.

In still another embodiment, the invention relates to an Extreme dark green color-conferring QTL or an Extreme dark green color-conferring part thereof, which is associated with at least a $1^{st}$ DNA marker represented by a $1^{st}$ pair of PCR oligonucleotide primers comprising forward primer of SEQ ID NO 1, reverse primer of SEQ ID NO 2 and probe of SEQ ID NO 9, and/or a at least a $2^{nd}$ DNA marker represented by a $2^{nd}$ pair of PCR primers comprising forward primer of SEQ ID NO 3, reverse primer of SEQ ID NO 4 and probe of SEQ ID NO 10, particularly said QTL or a functional part thereof is associated with said $1^{st}$ and $2^{nd}$ DNA marker.

In still another embodiment, the invention relates to an Extreme dark green color-conferring QTL or an Extreme dark green color-conferring part thereof, which and is associated with at least a $1^{st}$ DNA marker represented by a $1^{st}$ pair of PCR oligonucleotide primers comprising forward primer of SEQ ID NO 5, reverse primer of SEQ ID NO 6 and probe of SEQ ID NO 11, and a $2^{nd}$ pair of PCR primers comprising forward primer of SEQ ID NO 7, reverse primer of SEQ ID NO 8 and probe of SEQ ID NO 12, particularly said QTL or a functional part thereof is associated with said $1^{st}$ and $2^{nd}$ DNA marker.

The present invention also relates to the use of extreme dark green color propagating material obtainable from a pepper plant according to any of the preceding embodiments for growing a pepper plant in order to produce extreme dark green color fruit and harvest said extreme dark green color fruits wherein the said fruits are characterized, at immature harvestable stage, by the following physicochemical characteristics:
a. a content in Chlorophyll B greater than 6, particularly greater than 7, more particularly greater than 8 and even more particularly greater than 9 µg/g of fresh weight,
b. a content in Chlorophyll A greater than 20, particularly greater than 25, more particularly greater than 30 µg/g of fresh weight,
c. a content in lutein greater than 5, particularly greater than 6, more particularly greater than about 7 µg/g of fresh weight,
d. a content in violaxanthin greater than 2, particularly greater than 2.5, more particularly greater than 3, even more particularly greater than 3.5 µg/g of fresh weight, It is a further embodiment of the present invention to provide a method for increasing the content pigments of pepper fruits of pepper plant selected from the group comprising chlorophyll a, chlorophyll b, lutein and violaxanthin, comprising the steps of:
a) selecting a plant of the genus *Capsicum*, which exhibits Extreme dark green color, wherein said color related trait is associated with two QTL or a functional part thereof capable of directing or controlling expression of said extreme dark green color in the pepper fruit of the pepper plant, wherein said trait can be identified by the presence of the following molecular markers loci in the genome: SP436, SP626, SP693 and SP694 or
by any adjacent marker that is statistically correlated and thus co-segregates with the Extreme dark green color,
b) crossing said plant of step a), which exhibits Extreme dark green color, with a pepper plant, particularly a cultivated pepper plant, which does not exhibit extreme dark green color and exhibits lower content, as compared to the plant of step a), of all four of the pigments of pepper fruits of pepper plant selected from the group comprising chlorophyll A, chlorophyll B, lutein and violaxanthin
c) selecting progeny from said cross which exhibits extreme dark green color, increased content, as compared to the plant of step d), of all four of the pigments of pepper fruits of pepper plant selected from the group comprising chlorophyll a, chlorophyll b, lutein and violaxanthin and demonstrates association of the extreme dark green color with said at the four marker loci of step a).

It is a further embodiment of the present invention to provide a method for providing pepper plant producing pepper fruits exhibiting an increased content of chlorophyll a, chlorophyll b, lutein and violaxanthin, comprising the steps of:

d) selecting a plant of the genus *Capsicum*, which exhibits Extreme dark green color, wherein said trait is associated with two QTL, QTL1 and QTL2, or a functional part thereof capable of directing or controlling expression of said extreme dark green color in the pepper fruit of the pepper plant, wherein said QTL1 or a functional part thereof is genetically linked to marker loci SP436 and SP626 and wherein QTL2 or a functional part thereof is genetically linked to marker loci SP693 and SP694, which co-segregate with the Extreme dark green color and can be identified in a PCR reaction by i) forward primer of SEQ ID NO 1 reverse primer of SEQ ID NO 2 and probe of SEQ ID NO 9 for marker locus SP436;

ii) forward primer of SEQ ID NO 3, reverse primer of SEQ ID NO 4 and probe of SEQ ID NO 10, for marker locus SP626;

iii) forward primer of SEQ ID NO 5, reverse primer of SEQ ID NO 6 and probe of SEQ ID NO 11 for marker locus SP693;

iv) forward primer of SEQ ID NO 7, reverse primer of SEQ ID NO 8 and probe of SEQ ID NO 12 for marker locus SP694 or by any adjacent marker that is statistically correlated and thus co-segregates with the Extreme dark green color.

In one particular embodiment, the pepper plant according to the present invention, as described in any of the previous embodiments, is homozygous at the QTL1 and QTL2.

Based on the description of the present invention, the skilled person who is in possession of *Capsicum annuum*, line 8728C, seed of which has been deposited at NCIMB under No NCIMB 41858 on Jul. 29, 2011, or of a progeny or ancestor thereof containing the genetic determinants capable of directing or controlling the extreme dark green trait, as described herein, has no difficulty to transfer the said genetic determinants of the present invention to other pepper plants of various types using breeding techniques well-known in the art with the support of marker loci herein disclosed.

DEFINITIONS

The technical terms and expressions used within the scope of this application are generally to be given the meaning commonly applied to them in the pertinent art of (molecular) plant breeding and cultivation if not otherwise indicated herein below.

As used in this specification and the appended claims, the singular forms "a", "an", and "the" include plural referents unless the context clearly dictates otherwise. Thus, for example, reference to "a plant" includes one or more plants, and reference to "a cell" includes mixtures of cells, tissues, and the like.

A "cultivated pepper" plant is understood within the scope of the invention to refer to a plant that is no longer in the natural state but has been developed by human care and for human use and/or (commercial) growing purposes and/or consumption. "Cultivated pepper plants" are further understood to exclude those wild-type species which comprise the trait being subject of this invention as a natural trait and/or part of their natural genetics. Cultivated pepper plants also typically display favourable agronomical and fruit quality characteristics as well as resistance(s) to *Xanthomonas campestris* pv. *Vesicatoria*, and/or potyvirus, and/or CMV, and/or TMV, and/or TSWV virus, whereas non-cultivated plants do not.

The expression "immature harvestable stage" is understood herein to refer to a stage in the pepper fruit development where the fruit, having reached full physiological development (cell division and expansion being completed, fruit size and pericarp thickness having reached maximum values), has not yet gone through the ripening process.

The "ripening process" is associated with chloroplasts changing to chromoplasts, with chlorophyll degradation, carotenoid biosynthesis, seed maturation, and changes in the carbohydrate content of the pericarp.

A "genetic determinant directing or controlling expression" is understood herein to refer to a heritable genetic element that is capable of contributing to the darkness of the fruit color of the plant by influencing expression of this color trait on the level of the DNA itself, on the level of translation, transcription and/or activation of a final polypeptide product.

An "allele" is understood within the scope of the invention to refer to alternative or variant forms of various genetic units identical or associated with different forms of a gene or of any kind of identifiable genetic element, which are alternative in inheritance because they are situated at the same locus in homologous chromosomes. Such alternative or variant forms may be the result of single nucleotide polymorphisms, insertions, inversions, translocations or deletions, or the consequence of gene regulation caused by, for example, by chemical or structural modification, transcription regulation or post-translational modification/regulation. In a diploid cell or organism, the two alleles of a given gene or genetic element typically occupy corresponding loci on a pair of homologous chromosomes.

An allele associated with a qualitative trait may comprise alternative or variant forms of various genetic units including those that are identical or associated with a single gene or multiple genes or their products or even a gene disrupting or controlled by a genetic factor contributing to the phenotype represented by the locus.

As used herein, the term "allele" refers to an alternative or variant form of a genetic unit as defined herein above, when used as a marker to locate genetic loci containing alleles on a chromosome that contribute to variability of phenotypic traits.

As used herein, the term "breeding", and grammatical variants thereof, refer to any process that generates a progeny individual. Breeding can be sexual or asexual, or any combination thereof. Exemplary non-limiting types of breedings include crossings, selfing, doubled haploid derivative generation, and combinations thereof.

In the context of the present invention, the expression "established breeding population" or "population" refers to a collection of potential breeding partners produced by and/or used as parents in a breeding program; e.g., a commercial breeding program. The members of the established breeding population are typically well-characterized genetically and/or phenotypically. For example, several phenotypic traits of interest might have been evaluated, e.g., under different environmental conditions, at multiple locations, and/or at different times. Alternatively or in addition, one or more genetic loci associated with expression of the phenotypic traits might have been identified and one or more of the members of the breeding population might have been genotyped with respect to the one or more genetic loci as well as with respect to one or more genetic markers that are associated with the one or more genetic loci.

As used herein, the phrase "diploid individual" refers to an individual that has two sets of chromosomes, typically one from each of its two parents. However, it is understood that in some embodiments a diploid individual can receive its "maternal" and "paternal" sets of chromosomes from the same single organism, such as when a plant is selfed to produce a subsequent generation of plants.

"Homozygous" is understood within the scope of the invention to refer to like alleles at one or more corresponding loci on homologous chromosomes.

"Heterozygous" is understood within the scope of the invention to refer to unlike alleles at one or more corresponding loci on homologous chromosomes.

"Backcrossing" is understood within the scope of the invention to refer to a process in which a hybrid progeny is repeatedly crossed back to one of the parents. Different recurrent parents may be used in subsequent backcrosses.

"Locus" is understood within the scope of the invention to refer to a region on a chromosome, which comprises a gene or any other genetic element or factor contributing to a trait.

As used herein, "marker locus" refers to a region on a chromosome, which comprises a nucleotide or a polynucleotide sequence that is present in an individual's genome and that is associated with one or more loci of interest, which may which comprise a gene or any other genetic element or factor contributing to a trait. "Marker locus" also refers to a region on a chromosome, which comprises a polynucleotide sequence complementary to a genomic sequence, such as a sequence of a nucleic acid used as probes.

"Genetic linkage" or "linkage" or "association" is understood within the scope of the invention to refer to an association of characters in inheritance due to location of genes in proximity on the same chromosome, measured by percent recombination between loci (centi-Morgan, cM).

In the context of the present invention, the expression "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the phrases "sexually crossed" and "sexual reproduction" in the context of the presently disclosed subject matter refers to the fusion of gametes to produce progeny (e.g., by fertilization, such as to produce seed by pollination in plants). A "sexual cross" or "cross-fertilization" is in some embodiments fertilization of one individual by another (e.g., cross-pollination in plants). The term "selfing" refers in some embodiments to the production of seed by self-fertilization or self-pollination; i.e., pollen and ovule are from the same plant.

As used herein, the phrase "genetic marker" refers to a feature of an individual's genome (e.g., a nucleotide or a polynucleotide sequence that is present in an individual's genome) that is associated with one or more loci of interest. In some embodiments, a genetic marker is polymorphic in a population of interest, or the locus occupied by the polymorphism, depending on context. Genetic markers include, for example, single nucleotide polymorphisms (SNPs), indels (i.e., insertions/deletions), simple sequence repeats (SSRs), restriction fragment length polymorphisms (RFLPs), random amplified polymorphic DNAs (RAPDs), cleaved amplified polymorphic sequence (CAPS) markers, Diversity Arrays Technology (DArT) markers, and amplified fragment length polymorphisms (AFLPs), among many other examples. Genetic markers can, for example, be used to locate genetic loci containing alleles on a chromosome that contribute to variability of phenotypic traits. The phrase "genetic marker" can also refer to a polynucleotide sequence complementary to a genomic sequence, such as a sequence of a nucleic acid used as probes.

A genetic marker can be physically located in a position on a chromosome that is within or outside of to the genetic locus with which it is associated (i.e., is intragenic or extragenic, respectively). Stated another way, whereas genetic markers are typically employed when the location on a chromosome of the gene or of a functional mutation, e.g. within a control element outside of a gene, that corresponds to the locus of interest has not been identified and there is a non-zero rate of recombination between the genetic marker and the locus of interest, the presently disclosed subject matter can also employ genetic markers that are physically within the boundaries of a genetic locus (e.g., inside a genomic sequence that corresponds to a gene such as, but not limited to a polymorphism within an intron or an exon of a gene).

As used herein, the term "genotype" refers to the genetic constitution of a cell or organism. An individual's "genotype for a set of genetic markers" includes the specific alleles, for one or more genetic marker loci, present in the individual's haplotype. As is known in the art, a genotype can relate to a single locus or to multiple loci, whether the loci are related or unrelated and/or are linked or unlinked. In some embodiments, an individual's genotype relates to one or more genes that are related in that the one or more of the genes are involved in the expression of a phenotype of interest (e.g., a quantitative trait as defined herein). Thus, in some embodiments a genotype comprises a summary of one or more alleles present within an individual at one or more genetic loci of a quantitative trait. In some embodiments, a genotype is expressed in terms of a haplotype (defined herein below).

As used herein, the term "germplasm" refers to the totality of the genotypes of a population or other group of individuals (e.g., a species). The term "germplasm" can also refer to plant material; e.g., a group of plants that act as a repository for various alleles. The phrase "adapted germplasm" refers to plant materials of proven genetic superiority; e.g., for a given environment or geographical area, while the phrases "non-adapted germplasm," "raw germplasm," and "exotic germplasm" refer to plant materials of unknown or unproven genetic value; e.g., for a given environment or geographical area; as such, the phrase "non-adapted germplasm" refers in some embodiments to plant materials that are not part of an established breeding population and that do not have a known relationship to a member of the established breeding population.

As used herein, the terms "hybrid", "hybrid plant," and "hybrid progeny" refers to an individual produced from genetically different parents (e.g., a genetically heterozygous or mostly heterozygous individual).

As used herein, the phrase "single cross $F_1$ hybrid" refers to an $F_1$ hybrid produced from a cross between two inbred lines.

As used herein, the phrase "inbred line" refers to a genetically homozygous or nearly homozygous population. An inbred line, for example, can be derived through several cycles of brother/sister breedings or of selfing or in dihaploid production. In some embodiments, inbred lines breed true for one or more phenotypic traits of interest. An "inbred", "inbred individual", or "inbred progeny" is an individual sampled from an inbred line.

As used herein, the term "dihaploid line", refers to stable inbred lines issued from anther culture. Some pollen grains (haploid) cultivated on specific medium and circumstances can develop plantlets containing n chromosomes. These plantlets are then "doubled" and contain 2n chromosomes. The progeny of these plantlets are named "dihaploid" and are essentially not segregating any more (stable).

As used herein, the term "linkage", and grammatical variants thereof, refers to the tendency of alleles at different loci on the same chromosome to segregate together more often than would be expected by chance if their transmission were independent, in some embodiments as a consequence of their physical proximity.

As used herein, the phrase "nucleic acid" refers to any physical string of monomer units that can be corresponded to a string of nucleotides, including a polymer of nucleotides (e.g., a typical DNA, cDNA or RNA polymer), modified oligonucleotides (e.g., oligonucleotides comprising bases that are not typical to biological RNA or DNA, such as 2'-O-methylated oligonucleotides), and the like. In some embodiments, a nucleic acid can be single-stranded, double-stranded, multi-stranded, or combinations thereof. Unless otherwise indicated, a particular nucleic acid sequence of the presently disclosed subject matter optionally comprises or encodes complementary sequences, in addition to any sequence explicitly indicated.

As used herein, the phrase "phenotypic trait" refers to the appearance or other detectable characteristic of an individual, resulting from the interaction of its genome, proteome and/or metabolome with the environment.

As used herein, the term "plurality" refers to more than one. Thus, a "plurality of individuals" refers to at least two individuals. In some embodiments, the term plurality refers to more than half of the whole. For example, in some embodiments a "plurality of a population" refers to more than half the members of that population.

As used herein, the term "progeny" refers to the descendant(s) of a particular cross. Typically, progeny result from breeding of two individuals, although some species (particularly some plants and hermaphroditic animals) can be selfed (i.e., the same plant acts as the donor of both male and female gametes). The descendant(s) can be, for example, of the $F_1$, the $F_2$, or any subsequent generation.

As used herein, the phrase "quantitative trait" refers to a phenotypic trait that can be described numerically (i.e., quantitated or quantified). A quantitative trait typically exhibits continuous variation between individuals of a population; that is, differences in the numerical value of the phenotypic trait are slight and grade into each other. Frequently, the frequency distribution in a population of a quantitative phenotypic trait exhibits a bell-shaped curve (i.e., exhibits a normal distribution between two extremes).

A quantitative trait (QTL) is typically the result of a genetic locus interacting with the environment or of multiple genetic loci interacting with each other and/or with the environment. Examples of quantitative traits include plant height and yield.

For the purpose of the present invention, the term "co-segregation" refers to the fact that the allele for the trait and the allele(s) for the marker(s) tend to be transmitted together because they are physically close together on the same chromosome (reduced recombination between them because of their physical proximity) resulting in a non-random association of their alleles as a result of their proximity on the same chromosome. "Co-segregation" also refers to the presence of two or more traits within a single plant of which at least one is known to be genetic and which cannot be readily explained by chance.

As used herein, the terms "quantitative trait locus" (QTL) and "marker trait association" refer to an association between a genetic marker and a chromosomal region and/or gene that affects the phenotype of a trait of interest. Typically, this is determined statistically; e.g., based on one or more methods published in the literature. A QTL can be a chromosomal region and/or a genetic locus with at least two alleles that differentially affect a phenotypic trait (either a quantitative trait or a qualitative trait).

As used herein, the phrase "qualitative trait" refers to a phenotypic trait that is controlled by one or a few genes that exhibit major phenotypic effects. Because of this, qualitative traits are typically simply inherited. Examples in plants include, but are not limited to, flower color, and several known disease resistances such as, for example, Bacterial spot resistance or Tomato Mosaic Virus resistance.

"Marker-based selection" is understood within the scope of the invention to refer to e.g. the use of genetic markers to detect one or more nucleic acids from the plant, where the nucleic acid is associated with a desired trait to identify plants that carry genes for desirable (or undesirable) traits, so that those plants can be used (or avoided) in a selective breeding program.

"Microsatellite or SSRs (Simple sequence repeats) Marker" is understood within the scope of the invention to refer to a type of genetic marker that consists of numerous repeats of short sequences of DNA bases, which are found at loci throughout the plant's genome and have a likelihood of being highly polymorphic.

A single nucleotide polymorphism (SNP), a variation at a single site in DNA, is the most frequent type of variation in the genome. A single-nucleotide polymorphism (SNP) is a DNA sequence variation occurring when a single nucleotide—A, T, C, or G—in the genome (or other shared sequence) differs between members of a biological species or paired chromosomes in an individual. For example, two sequenced DNA fragments from different individuals, AAGCCTA to AAGCTTA, contain a difference in a single nucleotide. In this case there are two alleles: C and T. The basic principles of SNP array are the same as the DNA microarray. These are the convergence of DNA hybridization, fluorescence microscopy, and DNA capture. The three components of the SNP arrays are the array that contains nucleic acid sequences (i.e. amplified sequence or target), one or more labeled allele-specific oligonucleotide probes and a detection system that records and interprets the hybridization signal.

The presence or absence of the desired allele may be determined by real-time PCR using double-stranded DNA dyes or the fluorescent reporter probe method "PCR (Polymerase chain reaction)" is understood within the scope of the invention to refer to a method of producing relatively large amounts of specific regions of DNA or subset(s) of the genome, thereby making possible various analyses that are based on those regions.

"PCR primer" is understood within the scope of the invention to refer to relatively short fragments of single-stranded DNA used in the PCR amplification of specific regions of DNA.

"Phenotype" is understood within the scope of the invention to refer to a distinguishable characteristic(s) of a genetically controlled trait.

As used herein, the phrase "phenotypic trait" refers to the appearance or other detectable characteristic of an individual, resulting from the interaction of its genome, proteome and/or metabolome with the environment.

"Polymorphism" is understood within the scope of the invention to refer to the presence in a population of two or more different forms of a gene, genetic marker, or inherited trait or a gene product obtainable, for example, through alternative splicing, DNA methylation, etc.

"Selective breeding" is understood within the scope of the invention to refer to a program of breeding that uses plants that possess or display desirable traits as parents.

"Probe" as used herein refers to a group of atoms or molecules which is capable of recognising and binding to a specific target molecule or cellular structure and thus allowing detection of the target molecule or structure. Particularly, "probe" refers to a DNA or RNA sequence which is labelled and which can be used to detect the presence of and to quantitate a complementary sequence by molecular hybridization.

The term "hybridize" as used herein refers to conventional hybridization conditions, preferably to hybridization conditions at which 5×SSPE, 1% SDS, 1×Denhardts solution is used as a solution and/or hybridization temperatures are between 35° C. and 70° C., preferably 65° C. After hybridization, washing is preferably carried out first with 2×SSC, 1% SDS and subsequently with 0.2×SSC at temperatures between 35° C. and 75° C., particularly between 45° C. and 65° C., but especially at 59° C. (regarding the definition of SSPE, SSC and Denhardts solution see Sambrook et al. loc. cit.). High stringency hybridization conditions as for instance described in Sambrook et al, supra, are particularly preferred. Particularly preferred stringent hybridization conditions are for instance present if hybridization and washing occur at 65° C. as indicated above. Non-stringent hybridization conditions for instance with hybridization and washing carried out at 45° C. are less preferred and at 35° C. even less.

"Sequence Homology or Sequence Identity" is used herein interchangeably. The terms "identical" or percent "identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. If two sequences which are to be compared with each other differ in length, sequence identity preferably relates to the percentage of the nucleotide residues of the shorter sequence which are identical with the nucleotide residues of the longer sequence. As used herein, the percent identity/homology between two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described herein below. For example, sequence identity can be determined conventionally with the use of computer programs such as the Bestfit program (Wisconsin Sequence Analysis Package, Version 8 for Unix, Genetics Computer Group, University Research Park, 575 Science Drive Madison, Wis. 53711). Bestfit utilizes the local homology algorithm of Smith and Waterman, Advances in Applied Mathematics 2 (1981), 482-489, in order to find the segment having the highest sequence identity between two sequences. When using Bestfit or another sequence alignment program to determine whether a particular sequence has for instance 95% identity with a reference sequence of the present invention, the parameters are preferably so adjusted that the percentage of identity is calculated over the entire length of the reference sequence and that homology gaps of up to 5% of the total number of the nucleotides in the reference sequence are permitted. When using Bestfit, the so-called optional parameters are preferably left at their preset ("default") values. The deviations appearing in the comparison between a given sequence and the above-described sequences of the invention may be caused for instance by addition, deletion, substitution, insertion or recombination. Such a sequence comparison can preferably also be carried out with the program "fasta20u66" (version 2.0u66, September 1998 by William R. Pearson and the University of Virginia; see also W. R. Pearson (1990), Methods in Enzymology 183, 63-98, appended examples and http://workbench.sdsc.edu/). For this purpose, the "default" parameter settings may be used.

Another indication that two nucleic acid sequences are substantially identical is that the two molecules hybridize to each other under stringent conditions. The phrase: "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point for the specific sequence at a defined ionic strength and pH. Typically, under "stringent conditions" a probe will hybridize to its target subsequence, but to no other sequences.

The thermal melting point is the temperature (under defined ionic strength and pH) at which 50% of the target sequence hybridizes to a perfectly matched probe. Very stringent conditions are selected to be equal to the melting temperature ($T_m$) for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2 times SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1 times SSC at 45° C. for 15 minutes. An example low stringency wash for a duplex of, e.g., more than 100 nucleotides, is 4-6 times SSC at 40° C. for 15 minutes. For short probes (e.g., about 10 to 50 nucleotides), stringent conditions typically involve salt concentrations of less than about 1.0M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2 times (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g. when a copy of a nucleic acid is created using the maximum codon degeneracy permitted by the genetic code.

A "plant" is any plant at any stage of development, particularly a seed plant.

A "plant cell" is a structural and physiological unit of a plant, comprising a protoplast and a cell wall. The plant cell may be in form of an isolated single cell or a cultured cell, or as a part of higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" or "plant material obtainable from a plant" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

As used herein, the term "population" means a genetically heterogeneous collection of plants sharing a common genetic derivation As used herein, the term "pepper" means any variety, cultivar, or population of *Capsicum annuum*.

As used herein, the term "variety" or "cultivar" means a group of similar plants that by structural features and performance can be identified from other varieties within the same species.

As used herein, the expression "extreme dark green" characterizing the pepper fruits produced by the pepper plant of any of the embodiments and associated with any of the following expression "trait" or "locus" or "allele" or "QTL" means that the said fruits are characterized by the following physicochemical characteristics at immature harvestable stage:
  a. a content in Chlorophyll a greater than about 5, particularly greater than about 6, more particularly greater than about 7 µg/g of fresh weight,
  b. a content in Chlorophyll b greater than about 15, particularly greater than about 18, more particularly greater than about 20 µg/g of fresh weight,
  c. a content in lutein greater than about 5, particularly greater than about 6, particularly greater than about 7 µg/g of fresh weight,
  d. a content in violaxanthin greater than about 2.5, particularly greater than about 3, more particularly greater than about 3.5 µg/g of fresh weight,

SEED DEPOSIT DETAILS

The following seed samples were deposited with NCIMB, Ferguson Building, Craibstone Estate, Bucksburn, Aberdeen AB21 9YA, Scotland, UK, on Jul. 29, 2011 under the provisions of the Budapest Treaty in the name of Syngenta Participations AG:
  NCIMB 41858, *Capsicum annuum* 8728C.

EXAMPLES

Germplasm and Population Development

A breeding strategy was designed to identify the extreme dark green fruit color from pungent ancho chile peppers into sweet blocky peppers. An initial hybrid cross was made by crossing ancho 'San Luis' (extreme dark green source) with a blocky breeding line. The F1 from this cross was used to generate a segregating F2 population. F2 Individuals with the extreme dark green fruit color and blocky shape were selected based on visual appearance, followed by selfing and conventional pedigree selection for the extreme dark green trait for seven generations, to create stable fixed inbred lines. Stable extreme dark green inbred lines were testcrossed to one another to develop extreme dark green hybrid varieties. Isolation of the genetic factors responsible for extreme dark green was simultaneously pursued following a quantitative trait loci discovery approach. A mapping population was generated by crossing an extreme dark green inbred with a non-extreme dark green inbred. The resulting hybrid was used to generate a dihaploid population via anther culture. The segregating dihaploid population was phenotyped for the extreme dark green trait using a categorical scale to classify lines as extreme dark green or non-extreme dark green, and using colorimetry to obtain quantitative and objective color data for each line (see below material & methods) as well as using pigments content measurement. The categorical scale was based on visually matching fruit with color reference cards labeled from 1 (light) to 9 (dark), where 9 represented the extreme dark green phenotype.

An extreme dark green pepper plant *Capsicum annuum*, 8728C, producing fruit which at immature harvestable stage that exhibit violaxanthin, lutein, chlorophyll A and chlorophyll B contents according to the present invention has been retained and deposited at NCIMB under Number NCIMB 41858 on Jul. 29, 2011.

Plant 8728C was selfed and among the progeny, plants showing extreme dark green fruits were selfed again, and among that F2 population, extreme dark green double haploid plants were generated, and one of them was used as a parent for crossing with plant 8728C for generating hybrids, and among them RPP25965 which is an extreme dark green pepper.

Further characterization and definition of the trait was accomplished by screening a panel of germplasm ranging in phenotype from regular green to extreme dark green.

To this end, several green pepper varieties available on the market were used and evaluated by visual ranking with color reference, but also by colorimetry measurement and above all by measuring the content of those varieties in chlorophyll A, Chlorophyll B, lutein and violaxanthin as well as beta carotene.

The pepper varieties available on the market that were tested were: Crusader (Rogers), Encore (Rogers), Declaration (Harris Moran), Aristotle (Harris Seeds), Karisma (Harris Moran), Hunter (Rogers), Tomcat (Rogers), 8302 (Seminis), 7141 (Seminis) and 1819 (Seminis).

It has been determined that the color measurement by objective means with a colorimeter correlates with chlorophyll A&B, lutein and violaxanthin content. That is to say that the deeper the color is, the higher the content of the pepper fruits in those pigments.

Table 1 shows the correlation between colorimetry values and pigments content of the pepper fruits analyzed according to the present invention.

This clearly shows that the pigment content of the pepper fruits according to the present invention bearing the extreme dark green color trait relates to dark green color as evaluated by either subjective eye-visual perception or objective colorimetry.

Table 1 also shows the correlation between pigments contents and colorimeter values measured for pepper fruits of pepper plants according to the present invention grown in different areas, i.e. Gilroy (Calif., USA), Naples (Fla., USA) and El Ejido (Spain). From that Table it appears that the values of the different measured parameters are not affected by environmental conditions and thus shows that the phenotype of extreme dark green color, either evaluated by colorimeter measurement or by pigments contents is controlled by genetic determinants contained in the genome of the said plants.

Phenotyping

Fruit Color and Metabolite (Pigment) Measurements of a Germplasm Panel Representing Pepper Varieties with and without the Extreme Dark Green Trait Thirty six *C. annuum* varieties comprised of inbred lines and F1 hybrids were grown in summer 2010 in Gilroy, Calif. under standard field conditions, in autumn 2010/winter 2011 in El Ejido, Spain under standard passive greenhouse conditions, and in spring 2011 in Naples, Fla. under standard field conditions. This germplasm panel was assembled to allow direct comparisons of pepper germplasm with and without the extreme dark green trait and demonstrate that pepper plants with the extreme dark green trait are darker/more intense in green color with higher fruit pigment levels. Multiple trial locations were used to demonstrate the behavior of the trait across environments and growing conditions.

A randomized and replicated block design was used for laying out experimental plots, and a plot was treated as the experimental unit, with 5 random fruit selected to represent the plot. Samples from the 5 fruit were pooled for pigment measurements, and color data for the 5 fruit were summarized to provide a representative data set for the variety and replicate.

Materials and Methods

Environmental conditions, including light source, object size, color background, and angle of vision or illumination can affect how a colored object appears to a human observer. In order to overcome this subjectivity, color measurement systems and instruments have been developed for quantifying colors and expressing colors in terms of three variables which completely and uniquely describe the color. A complete discussion of color measurement theory can be found in:

Berns, R. 2000. Billmeyer and Saltzman's principles of color technology. Wiley.

Malacara, D. 2002. Color vision and colorimetry theory and applications. SPIE Press.

To measure fruit color, two experimental methodologies were used, colorimetry/spectrophotometry, and image analysis via a computer vision system. To measure fruit pigment contents, reversed phase liquid chromatography and UV DAD detection were used.

Colorimetry/Spectrophotometry

A Konica Minolta colorimeter model CR-400 was used in California and Florida to generate color data on pepper fruits, using the CIELAB L*a*b* color space, C illuminant, and 2 degree angle of observer. The colorimeter was operated using the 8 mm aperture measuring head and Spectramagic NX software version 1.9. A Konica Minolta handheld spectrophotometer model CM-2500d with 8 mm measurement aperture was used in Spain to generate color data on pepper fruits, using the CIELAB L*a*b* color space, C and D65 illuminant, and 10 degree angle of observer. The spectrophotometer was operated using Spectramagic NX software version 3.6. In all three locations, the instrument was calibrated prior to and during use according to the manufacturer's instructions. Fruit samples were harvested from each plot at immature (e.g. unripe, fully physiologically developed) stage and brought to the lab for further processing. The surface of each fruit was cleaned by gently wiping with a damp paper towel to remove any dirt or debris. The measurement aperture was then held in tight connection against the surface of the fruit, to ensure no infiltration of external sources of light, and three measurements were taken, moving the aperture to three random representative spots on the fruit surface between measurements.

The CIELAB color scale is used widely by the food industry to measure color and demonstrate differences in color. The scale includes 3 data variables, L*, a*, and b*. L* indicates lightness on a 0 to 100 scale, where 0 is black and 100 is white. The variables a* and b* indicate the amount of red, green, blue, and yellow color: +a* is the red direction, −a* is the green direction, +b* is the yellow direction, and −b* is the blue direction. Differences in color between two samples can be expressed in terms of the change in L*, a*, and/or b*.

Image Analysis

Computer vision systems (CVS) can be used to measure the whole distribution of color on a fruit surface, by translating the RGB pixel colors of a digital sample image into CIELAB L*a*b* values. Algorithms used by the image analysis software correct for the cameras' own color characteristics, fruit glossiness and fruit curvature, and calibrate the system.

CVS systems were used in California, Florida, and Spain to generate color data on pepper fruits. The systems consisted of the following hardware and software components:

Camera, Canon EOS Digital Rebel XT (Florida and California); EOS 450D (Spain)

Standardized lighting system, Westcott SpiderliteTD5 Location Kit with Westcott 27W/110V Daylt FLOU lamps X-Rite Digital Color Checker SG card for color calibration Lastolite EZY grey balance card, for white balance calibration Photoflex medium LiteRoom table top shooting white tent Flocked paper (Savage) and velvet fabric photographic background Image version (1.45)

Color transformer plug-in for ImageJ; Macro programs to automate image processing Photography was conducted in a room with no windows to ensure that the lighting system was the only source of illumination. Lamps were placed at equal distances from the sample platform and equal heights from the floor to center of the back of the light head. Lamp heads were angled at 45 degrees to the sample platform. Prior to taking photographs, lamps were turned on and allowed to warm up for at least 10 minutes. The background material was placed on the sample platform and the white tent placed on top of the background, with zipper opening facing out. The camera was mounted on a stand with the lens pointing down and positioned over the tent, at a fixed distance from the top of the table.

The camera was manually calibrated for white balance (uniformity of illumination within the photo field) and color at the beginning of each sample evaluation day. The same fruit samples used for collection of color data via colorimeter/spectrophotometer were used for the CVS and were placed inside the tent on the background. Fruits were spaced evenly in the photo field, not touching each other and not in the shadows of one another, and the tent was closed. The photographs were taken through an opening in the top of the tent. Photographs were processed using the ImageJ software program, version 1.95, and a proprietary macro developed for automation of the processing. Pixels in the digital photographs were identified by the software as either background or sample, and the RGB color values of each sample pixel were translated by the software into CIELAB L*a*b* color values using a color calibration algorithm. The macro then calculated summary statistics for all the color values of the sample pixels in each photograph of fruit samples.

Reversed Phase Liquid Chromatography and UV DAD Detection

The same fruit sample used for color analysis via colorimetry/spectrophotometry and image analysis was further analyzed for pigment content. Each of the five fruits comprising a sample was cut into pieces, removing and discarding the peduncle, seeds, and placental tissue, leaving only the pericarp. Pericarp pieces were combined in a blender (Waring model 61BL30) and processed to form a homogenous puree. An antifoaming agent (Silicone Anti-foam SAG 1572), 10 µL to 100 g pepper, was added to the blended puree to prevent splitting into aqueous and foam layers and to keep the pepper puree homogeneous during subsampling. 1.5 mL aliquots of the homogenized pepper pericarp were sub-sampled into 3.5 mL cryo vials, which were flash-frozen in liquid nitrogen and stored at −80° C. until analysis. Frozen puree samples were freeze dried and milled, then extracted twice with tert-buthyl-methyl-ether (TBME) and twice with methanol. Extracts were analyzed and separated into pigment components using an Agilent 1100 HPLC with binary pump and YMC C30 column. The injection volume was 10 µL (standard injection) and eluent flow was 0.5 mL/minute. Detection was via UV DAD.

Data Processing

Chromatograms were processed using Agilent Chemstation® software, to integrate and identify peaks. UV spectra were checked for each peak against that of library spectra before the identification was accepted. For quantitation the response factor of the calibrated reference compounds was calculated and used for the non-calibrated peaks.

FIGURES

FIG. 1 shows the content in Violaxanthin in µg/g of fresh (average value with 95% CI) weight for different entries that were grown in Gilroy.

FIG. 2 shows the content in Lutein in µg/g of fresh (average value with 95% CI) weight for different entries that were grown in Gilroy.

FIG. 3 shows the content in Chlorophyll A in µg/g of fresh (average value with 95% CI) weight for different entries that were grown in Gilroy.

FIG. 4 shows the content in Chlorophyll B in µg/g of fresh (average value with 95% CI) weight for different entries that were grown in Gilroy.

FIG. 5 shows the content in beta-carotene in µg/g of fresh (average value with 95% CI) weight for different entries that were grown in Gilroy.

FIG. 6 shows the L* value measured by colorimeter for different entries that were grown in Gilroy.

FIG. 7 shows the a* value for different entries that were grown in Gilroy.

FIG. 8 shows the b* value for different entries that were grown in Gilroy.

SEQUENCES

SEQ ID NO: 1
5' AGATATTCCCTCCCTCTTCATTATTCCT 3'

SEQ ID NO: 2
5' GAGGCTGCACGAACAGATCA 3'

SEQ ID NO: 3
5' GTGAAGGAAGCGTGATGAATGG 3'

SEQ ID NO: 4
5' CCTAACAGCACTTCAGGTGCAA 3'

SEQ ID NO: 5
5' ACGAGGATGCAACTGACTCAAAA 3'

SEQ ID NO: 6
5' CCCAAGTCACTAGGTTGTTGATTCT 3'

SEQ ID NO: 7
5' TCTTATTGGAGCAAAGAATAACTGGGTTAT 3'

SEQ ID NO: 8
5' TGCACTCTATGTGTTTGATATTTTGTCTCA 3'

SEQ ID NO: 9
5' CTGGAGTTACCAGTTTATA 3'

SEQ ID NO: 10
5' TAGTACGGTGTGCCAACAA 3'

SEQUENCES

SEQ ID NO: 11
5' ATGATGCGAATGGTCA 3'

SEQ ID NO: 12
5' TGTAGCTTCAATCTATTTGTTC 3'

Genotyping and QTL Discovery

A bi-parental population of 188 fixed lines was developed for the purpose of QTL mapping. The population was genotyped with a set of genome wide markers. The QTL analysis following standard practice was done with QTL Cartographer software. Raw phenotypic data was used in the analysis.

Two QTL (QTL1 and QTL2) were identified at <0.01% significance with markers, SP436 & SP626 on the one hand and SP693 & SP694 on the other hand, showing the highest association (linkage) with QTL1 and QTL2 respectively.

QTL 1

Marker locus SP 436
Forward primer:
(SEQ ID NO: 1)
5' AGATATTCCCTCCCTCTTCATTATTCCT 3'

Reverse primer:
(SEQ ID NO: 2)
5' GAGGCTGCACGAACAGATCA 3'

Extreme dark green allele specific probe:
(SEQ ID NO 9)
5' CTGGAGTTACCAGTTTATA 3'
Probe sequence was labelled with FM at the 5' end and with MGB-NFQ at the 3' end Marker locus SP626
Forward primer:
(SEQ ID NO: 3)
5' GTGAAGGAAGCGTGATGAATGG 3'

Reverse primer:
(SEQ ID NO: 4)
5' CCTAACAGCACTTCAGGTGCAA 3'

Extreme dark green allele specific probe:
(SEQ ID NO 10)
5' TAGTACGGTGTGCCAACAA 3'.
Probe sequence was labelled with VC at the 5' end and with MGB-NFQ at the 3' end.

QTL2

Marker locus SP693
Forward primer:
(SEQ ID NO: 5)
5' ACGAGGATGCAACTGACTCAAAA 3'

Reverse primer:
(SEQ ID NO: 6)
5' CCCAAGTCACTAGGTTGTTGATTCT 3'

3' Extreme dark green allele specific probe:
(SEQ ID NO 11)
5' ATGATGCGAATGGTCA 3'
Probe sequence was labelled with VC at the 5' end and with MGB-NFQ at the 3' end.

Marker locus SP694
Forward primer:
(SEQ ID NO: 7)
5' TCTTATTGGAGCAAAGAATAACTGGGTTAT 3'

Reverse primer:
(SEQ ID NO: 8)
5' TGCACTCTATGTGTTTGATATTTTGTCTCA 3'

Extreme dark green allele specific probe:
(SEQ ID NO 12)
5' TGTAGCTTCAATCTATTTGTTC 3'
Probe sequence was labelled with VC at the 5' end and with MGB-NFQ at the 3' end.

TABLE 2 shows the content in violaxanthin, Chlorophyll A and Chlorophyll B, lutein and beta-carotene for the various pepper plants chosen for the trials as well as plant 8728C and hybrid RPP25965. This table also shows the different colorimeter values of those plants. It clearly shows that the plant according to the inventions are different from existing blocky pepper varieties available on the market and do clearly differentiate from those.

Table 3 also shows a QTL validation of the extreme dark green color trait according to the present invention. Various individuals, including Double haploid plant derived from the population generated for QTL discovery, with different genetic profiles, either none of the QTL according to the present invention, only one, or both of QTL1 and QTL2 of the present invention.

Results of Table 3 clearly show the contribution of both QTL1 and QTL2 to the pigments content. It appears that both QTL lead to the increased content of violaxanthin, lutein, chlorophyll A and Chlorophyll B to the levels required by the present invention.

TABLE 1

|  | Violaxanthin - Gilroy | Lutein - Gilroy | Chlorophyll A - Gilroy | Chlorophyll B - Gilroy | b-carotene - Gilroy | L*(C) - Gilroy | a*(C) - Gilroy | b*(C) - Gilroy |
| --- | --- | --- | --- | --- | --- | --- | --- | --- |
| Violaxanthin - Gilroy | 1 | | | | | | | |
| Lutein - Gilroy | 0.95 | 1 | | | | | | |
| Chlorophyll A - Gilroy | 0.96 | 0.99 | 1 | | | | | |
| Chlorophyll B - Gilroy | 0.96 | 1.00 | 1.00 | 1 | | | | |
| b-carotene - Gilroy | 0.97 | 0.97 | 0.99 | 0.98 | 1 | | | |
| L*(C) - Gilroy | −0.79 | −0.80 | −0.76 | −0.79 | −0.73 | 1 | | |
| a*(C) - Gilroy | 0.75 | 0.87 | 0.82 | 0.85 | 0.77 | −0.76 | 1 | |
| b*(C) - Gilroy | −0.74 | −0.86 | −0.80 | −0.83 | −0.76 | 0.77 | −0.99 | 1 |
| Violaxanthin - El Ejido | 0.93 | 0.93 | 0.94 | 0.94 | 0.93 | −0.76 | 0.75 | −0.72 |
| Lutein - El Ejido | 0.90 | 0.95 | 0.93 | 0.94 | 0.90 | −0.84 | 0.85 | −0.84 |
| Chlorophyll A - El Ejido | 0.92 | 0.96 | 0.95 | 0.96 | 0.93 | −0.82 | 0.84 | −0.82 |
| Chlorophyll B - El Ejido | 0.91 | 0.95 | 0.94 | 0.95 | 0.91 | −0.84 | 0.84 | −0.83 |
| b-carotene - El Ejido | 0.93 | 0.95 | 0.96 | 0.96 | 0.95 | −0.77 | 0.79 | −0.77 |
| L*(C) - El Ejido | −0.66 | −0.77 | −0.72 | −0.75 | −0.67 | 0.82 | −0.87 | 0.88 |
| a*(C) - El Ejido | 0.70 | 0.79 | 0.73 | 0.77 | 0.68 | −0.81 | 0.92 | −0.92 |
| b*(C) - El Ejido | −0.69 | −0.78 | −0.72 | −0.75 | −0.67 | 0.80 | −0.92 | 0.92 |

TABLE 1-continued

| | | | | | | | | |
|---|---|---|---|---|---|---|---|---|
| Violaxanthin - Naples | 0.97 | 0.94 | 0.95 | 0.95 | 0.96 | −0.76 | 0.75 | −0.73 |
| Lutein - Naples | 0.96 | 0.98 | 0.98 | 0.99 | 0.97 | −0.81 | 0.85 | −0.84 |
| Chlorophyll A - Naples | 0.97 | 0.98 | 0.99 | 0.98 | 0.98 | −0.78 | 0.80 | −0.78 |
| Chlorophyll B - Naples | 0.97 | 0.98 | 0.99 | 0.99 | 0.98 | −0.80 | 0.81 | −0.80 |
| b-carotene - Naples | 0.97 | 0.95 | 0.97 | 0.96 | 0.98 | −0.75 | 0.76 | −0.74 |
| L*(C) - Naples | −0.69 | −0.80 | −0.75 | −0.78 | −0.69 | 0.84 | −0.82 | 0.82 |
| a*(C) - Naples | 0.80 | 0.81 | 0.78 | 0.81 | 0.74 | −0.87 | 0.87 | −0.86 |
| b*(C) - Naples | −0.79 | −0.81 | −0.77 | −0.80 | −0.74 | 0.88 | −0.88 | 0.88 |

| | Violaxanthin - El Ejido | Lutein - El Ejido | Chlorophyll A - El Ejido | Chlorophyll B - El Ejido | b-carotene - El Ejido | L*(C) - El Ejido | a*(C) - El Ejido | b*(C) - El Ejido |
|---|---|---|---|---|---|---|---|---|
| Violaxanthin - El Ejido | 1 | | | | | | | |
| Lutein - El Ejido | 0.96 | 1 | | | | | | |
| Chlorophyll A - El Ejido | 0.98 | 0.99 | 1 | | | | | |
| Chlorophyll B - El Ejido | 0.97 | 1.00 | 1.00 | 1 | | | | |
| b-carotene - El Ejido | 0.99 | 0.97 | 0.99 | 0.97 | 1 | | | |
| L*(C) - El Ejido | −0.70 | −0.81 | −0.78 | −0.79 | −0.73 | 1 | | |
| a*(C) - El Ejido | 0.73 | 0.84 | 0.82 | 0.84 | 0.75 | −0.89 | 1 | |
| b*(C) - El Ejido | −0.71 | −0.82 | −0.80 | −0.82 | −0.74 | 0.88 | −0.99 | 1 |
| Violaxanthin - Naples | 0.91 | 0.88 | 0.91 | 0.90 | 0.92 | −0.65 | 0.69 | −0.68 |
| Lutein - Naples | 0.92 | 0.93 | 0.96 | 0.95 | 0.94 | −0.74 | 0.78 | −0.77 |
| Chlorophyll A - Naples | 0.94 | 0.92 | 0.95 | 0.94 | 0.95 | −0.70 | 0.73 | −0.72 |
| Chlorophyll B - Naples | 0.95 | 0.94 | 0.96 | 0.95 | 0.96 | −0.72 | 0.75 | −0.74 |
| b-carotene - Naples | 0.91 | 0.88 | 0.92 | 0.90 | 0.93 | −0.65 | 0.68 | −0.68 |
| L*(C) - Naples | −0.73 | −0.83 | −0.79 | −0.81 | −0.74 | 0.77 | −0.77 | 0.76 |
| a*(C) - Naples | 0.77 | 0.84 | 0.83 | 0.85 | 0.77 | −0.82 | 0.90 | −0.89 |
| b*(C) - Naples | −0.76 | −0.84 | −0.82 | −0.84 | −0.76 | 0.83 | −0.91 | 0.91 |

| | Violaxanthin - Naples | Lutein - Naples | Chlorophyll A - Naples | Chlorophyll B - Naples | b-carotene - Naples | L*(C) - Naples | a*(C) - Naples | b*(C) - Naples |
|---|---|---|---|---|---|---|---|---|
| Violaxanthin - Naples | 1 | | | | | | | |
| Lutein - Naples | 0.97 | 1 | | | | | | |
| Chlorophyll A - Naples | 0.97 | 0.99 | 1 | | | | | |
| Chlorophyll B - Naples | 0.97 | 0.99 | 1.00 | 1 | | | | |
| b-carotene - Naples | 0.98 | 0.98 | 0.99 | 0.98 | 1 | | | |
| L*(C) - Naples | −0.70 | −0.79 | −0.73 | −0.76 | −0.69 | 1 | | |
| a*(C) - Naples | 0.79 | 0.84 | 0.80 | 0.82 | 0.77 | −0.76 | 1 | |
| b*(C) - Naples | −0.78 | −0.84 | −0.79 | −0.81 | −0.76 | 0.78 | −0.99 | 1 |

TABLE 2

| Entry | Violaxanthin | Lutein | Chlorophyll A | Chlorophyll B | b-carotene |
|---|---|---|---|---|---|
| Crusader | 1.87 | 4.08 | 20.6 | 5.54 | 1.20 |
| Encore | 1.42 | 3.51 | 17.6 | 4.67 | 1.07 |
| 8302 | 1.80 | 4.74 | 21.7 | 6.09 | 1.25 |
| 7141 | 1.77 | 5.20 | 24.6 | 6.83 | 1.44 |
| 1819 | 1.57 | 4.30 | 20.5 | 5.69 | 1.23 |
| Declaration | 1.65 | 3.60 | 17.9 | 4.85 | 1.11 |
| Aristotle | 1.61 | 3.45 | 17.5 | 4.70 | 1.12 |
| Karisma | 1.92 | 4.28 | 19.5 | 5.43 | 1.18 |
| Hunter | 1.98 | 4.24 | 21.0 | 5.89 | 1.17 |
| Tomcat | 2.04 | 4.27 | 21.1 | 5.89 | 1.23 |
| RPP 25965 | 4.37 | 8.04 | 33.8 | 10.50 | 1.76 |
| 8728C | 4.53 | 9.81 | 42.8 | 13.34 | 2.19 |
| Standard Deviation | 0.41 | 0.63 | 3.0 | 0.82 | 0.17 |
| F-test Probability | 0.0% | 0.0% | 0.0% | 0.0% | 0.0% |
| 5% LSD | 0.67 | 1.03 | 4.8 | 1.34 | 0.28 |

| Entry | L*(C) | a*(C) | b*(C) |
|---|---|---|---|
| Crusader | 38.3 | −10.6 | 13.5 |
| Encore | 40.7 | −11.7 | 16.2 |
| 8302 | 37.6 | −7.6 | 8.2 |
| 7141 | 38.2 | −8.2 | 8.6 |
| 1819 | 40.7 | −9.5 | 11.3 |
| Declaration | 40.7 | −9.7 | 11.7 |
| Aristotle | 40.9 | −10.1 | 12.4 |
| Karisma | 40.4 | −9.8 | 12.0 |
| Hunter | 36.5 | −8.9 | 10.3 |
| Tomcat | 37.8 | −9.9 | 12.3 |
| RPP 25965 | 34.4 | −5.1 | 4.3 |
| 8728C | 33.7 | −4.4 | 3.3 |
| Standard Deviation | 0.8 | 0.6 | 1.1 |
| F-test Probability | 0.0% | 0.0% | 0.0% |
| 5% LSD | 1.4 | 1.0 | 1.7 |

TABLE 3

| Entry | Violaxanthin | Lutein | Chlorophyll A | Chlorophyll B | b-carotene |
|---|---|---|---|---|---|
| 8728C, (QTL1 + QTL2) | 3.01 | 7.03 | 40.97 | 12.80 | 2.09 |
| 11498, (no QTL) | 1.09 | 1.97 | 14.23 | 3.92 | 0.92 |
| DH 16, (QTL1 + QTL2) | 2.40 | 6.53 | 37.38 | 11.70 | 1.88 |
| DH54, (QTL1) | 2.20 | 4.91 | 30.43 | 8.71 | 1.74 |
| DH69, (QTL2) | 1.91 | 4.59 | 27.88 | 7.98 | 1.64 |
| DH 11, (no QTL) | 1.16 | 3.12 | 20.48 | 5.66 | 1.24 |
| Standard Deviation | 0.37 | 0.72 | 3.98 | 1.15 | 0.25 |
| F-test Probability | 0.0% | 0.0% | 0.0% | 0.0% | 0.0% |
| 5% LSD | 0.59 | 1.17 | 6.47 | 1.88 | 0.40 |

| Entry | L*(C) | a*(C) | b*(C) |
|---|---|---|---|
| 8728C, (QTL1 + QTL2) | 36.99 | −4.74 | 3.84 |
| 11498, (no QTL) | 43.33 | −9.76 | 13.13 |
| DH 16, (QTL1 + QTL2) | 37.45 | −4.34 | 3.51 |

TABLE 3-continued

| | | | |
|---|---|---|---|
| DH54, (QTL1) | 38.26 | −6.83 | 6.54 |
| DH69, (QTL2) | 40.45 | −8.39 | 9.93 |
| DH 11, (no QTL) | 42.35 | −9.64 | 12.18 |

TABLE 3-continued

| | | | |
|---|---|---|---|
| Standard Deviation | 1.28 | 0.88 | 1.68 |
| F-test Probability | 0.0% | 0.0% | 0.0% |
| 5% LSD | 2.09 | 1.44 | 2.73 |

The invention claimed is:

1. A blocky fruit type *Capsicum annuum* pepper plant bearing extreme dark green color fruit at immature harvestable stage, said plant comprising two genetic determinants directing or controlling expression of said extreme dark green color in the pepper fruit of the pepper plant wherein said two genetic determinants are represented by two QTL,
   wherein the said genetic determinants are the genetic determinants of *Capsicum annuum* 8728C, seed of which has been deposited under Deposit Number NCIMB 41858 on Jul. 29, 2011,
   wherein the first QTL, QTL1, is genetically or physically linked to marker loci SP436 and SP626, and the second QTL, QTL2, is genetically or physically linked to marker loci SP693 and SP694, and
   wherein said pepper plant is homozygous at QTL1 and QTL2, and
   wherein the extreme dark green color is associated with the following physicochemical characteristics of the pepper fruits at immature harvestable stage:
      a content in Chlorophyll B greater than 6 µg/g of fresh weight,
      a content in Chlorophyll A greater than 20 µg/g of fresh weight,
      a content in lutein greater than 5 µg/g of fresh weight, and
      a content in violaxanthin greater than 2 µg/g of fresh weight.

2. A blocky fruit type pepper plant according to claim 1, wherein said QTL1 or a functional part thereof is genetically linked to two marker loci and wherein:
   i. marker locus SP436 can be identified in a PCR by amplification of a DNA fragment with the pair of oligonucleotide primers: forward primer of SEQ ID NO: 1 and reverse primer of SEQ ID NO: 2 and probe SEQ ID NO 9,
   ii. marker locus SP626 can be identified in a PCR by amplification of a DNA fragment with the pair of oligonucleotide primers: forward primer of SEQ ID NO: 3 and reverse primer of SEQ ID NO: 4 and probe SEQ ID NO 10,
   and wherein said QTL2 is genetically linked to two marker loci, and wherein:
   i. marker locus SP693 can be identified in a PCR by amplification of a DNA fragment with the pair of oligonucleotide primers: forward primer of SEQ ID NO: 5 and reverse primer of SEQ ID NO: 6 and probe SEQ ID NO 11,
   ii. marker locus SP694 can be identified in a PCR by amplification of a DNA fragment with the pair of oligonucleotide primers: forward primer of SEQ ID NO: 7 and reverse primer of SEQ ID NO: 8 and probe SEQ ID NO 12.

* * * * *

SEQUENCE LISTING

<160> NUMBER OF SEQ ID NOS: 12

<210> SEQ ID NO 1
<211> LENGTH: 28
<212> TYPE: DNA
<213> ORGANISM: Artificial Sequence
<220> FEATURE:
<223> OTHER INFORMATION: Marker locus SP 436 forward primer

<400> SEQUENCE: 1
agatattccc tccctcttca ttattcct                                28

<210> SEQ ID NO 2
<211> LENGTH: 20
<212> TYPE: DNA
<213> ORGANISM: Artificial Sequence
<220> FEATURE:
<223> OTHER INFORMATION: Marker locus SP 436 reverse primer

<400> SEQUENCE: 2
gaggctgcac gaacagatca                                         20

<210> SEQ ID NO 3
<211> LENGTH: 22
<212> TYPE: DNA
<213> ORGANISM: Artificial Sequence
<220> FEATURE:
<223> OTHER INFORMATION: Marker locus SP626 forward primer

<400> SEQUENCE: 3
gtgaaggaag cgtgatgaat gg                                      22

<210> SEQ ID NO 4
<211> LENGTH: 22
<212> TYPE: DNA
<213> ORGANISM: Artificial Sequence
<220> FEATURE:
<223> OTHER INFORMATION: Marker locus SP626 reverse primer

<400> SEQUENCE: 4
cctaacagca cttcaggtgc aa                                      22

<210> SEQ ID NO 5
<211> LENGTH: 23
<212> TYPE: DNA
<213> ORGANISM: Artificial Sequence
<220> FEATURE:
<223> OTHER INFORMATION: Marker locus SP693 forward primer

<400> SEQUENCE: 5
acgaggatgc aactgactca aaa                                     23

<210> SEQ ID NO 6
<211> LENGTH: 25
<212> TYPE: DNA
<213> ORGANISM: Artificial Sequence
<220> FEATURE:
<223> OTHER INFORMATION: Marker locus SP693 reverse primer -continued

<400> SEQUENCE: 6
cccaagtcac taggttgttg attct                                    25

<210> SEQ ID NO 7
<211> LENGTH: 30
<212> TYPE: DNA
<213> ORGANISM: Artificial Sequence
<220> FEATURE:
<223> OTHER INFORMATION: Marker locus SP694 forward primer

<400> SEQUENCE: 7
tcttattgga gcaaagaata actgggttat                               30

<210> SEQ ID NO 8
<211> LENGTH: 30
<212> TYPE: DNA
<213> ORGANISM: Artificial Sequence
<220> FEATURE:
<223> OTHER INFORMATION: Marker locus SP694 reverse primer

<400> SEQUENCE: 8
tgcactctat gtgtttgata ttttgtctca                               30

<210> SEQ ID NO 9
<211> LENGTH: 19
<212> TYPE: DNA
<213> ORGANISM: Artificial Sequence
<220> FEATURE:
<223> OTHER INFORMATION: Extreme dark green allele specific probe
      (marker locus SP 436)

<400> SEQUENCE: 9
ctggagttac cagtttata                                           19

<210> SEQ ID NO 10
<211> LENGTH: 19
<212> TYPE: DNA
<213> ORGANISM: Artificial Sequence
<220> FEATURE:
<223> OTHER INFORMATION: Extreme dark green allele specific probe
      (marker locus SP626)

<400> SEQUENCE: 10
tagtacggtg tgccaacaa                                           19

<210> SEQ ID NO 11
<211> LENGTH: 16
<212> TYPE: DNA
<213> ORGANISM: Artificial Sequence
<220> FEATURE:
<223> OTHER INFORMATION: Extreme dark green allele specific probe
      (marker locus SP693)

<400> SEQUENCE: 11
atgatgcgaa tggtca                                              16

<210> SEQ ID NO 12
<211> LENGTH: 22
<212> TYPE: DNA

```
<213> ORGANISM: Artificial Sequence
<220> FEATURE:
<223> OTHER INFORMATION: Extreme dark green allele specific probe
      (marker locus SP694)

<400> SEQUENCE: 12
tgtagcttca atctatttgt tc                                              22
```